(12) United States Patent
Wachsman et al.

(10) Patent No.: US 11,878,953 B2
(45) Date of Patent: Jan. 23, 2024

(54) SYSTEMS, METHODS, AND DEVICES FOR METHANE CONVERSION VIA GAS RECYCLING

(71) Applicant: UNIVERSITY OF MARYLAND, COLLEGE PARK, College Park, MD (US)

(72) Inventors: Eric D. Wachsman, Fulton, MD (US); Dongxia Liu, Clarksville, MD (US); Mann Sakbodin, Bangkok (TH)

(73) Assignee: UNIVERSITY OF MARYLAND, COLLEGE PARK, College Park, MD (US)

( * ) Notice: Subject to any disclaimer, the term of this patent is extended or adjusted under 35 U.S.C. 154(b) by 0 days.

(21) Appl. No.: 17/746,229

(22) Filed: May 17, 2022

(65) Prior Publication Data
US 2022/0363612 A1 Nov. 17, 2022

Related U.S. Application Data
(60) Provisional application No. 63/189,672, filed on May 17, 2021.

(51) Int. Cl.
*C07C 2/84* (2006.01)
*B01J 21/08* (2006.01)
(Continued)

(52) U.S. Cl.
CPC ............... *C07C 2/84* (2013.01); *B01J 10/00* (2013.01); *B01J 19/0053* (2013.01);
(Continued)

(58) Field of Classification Search
CPC . C07C 2/84; C07C 2521/08; C07C 2523/745; B01J 10/00; B01J 19/0053;
(Continued)

(56) References Cited

U.S. PATENT DOCUMENTS 10,525,407 B2   1/2020   Wachsman et al.
2021/0379549 A1  12/2021  Liu et al.

FOREIGN PATENT DOCUMENTS

WO    WO-2017062663 A1 *  4/2017  ............. B01D 53/32

OTHER PUBLICATIONS

Ashcroft et al., "Selective oxidation of methane to synthesis gas using transition metal catalysts," *Nature*, Mar. 1990, 344: pp. 319-321. (3 pages).
(Continued)

*Primary Examiner* — Thuan D Dang
(74) *Attorney, Agent, or Firm* — RowanTree Law Group, PLLC; Frederick F. Rosenberger

(57) ABSTRACT

In a first stage of a methane conversion system, at least some methane ($CH_4$) in an input gas flow stream can be converted into $C_2$ hydrocarbons, hydrogen gas ($H_2$), and aromatics to provide a first processed stream. The conversion can be direct non-oxidative methane conversion (DNMC). At least some of the aromatics can be removed from the first processed stream to provide a second processed stream. In a second stage of the methane conversion system, at least some of the $H_2$ can be removed from the second processed stream to provide a recycle stream. The recycle stream can be returned to the first stage of the methane conversion system for further conversion of methane and removal of aromatics and $H_2$ products.

20 Claims, 17 Drawing Sheets
(11 of 17 Drawing Sheet(s) Filed in Color)

(51) Int. Cl.
    B01J 19/00      (2006.01)
    B01J 19/18      (2006.01)
    B01J 23/745     (2006.01)
    B01J 10/00      (2006.01)
(52) U.S. Cl.
    CPC .......... B01J 19/1893 (2013.01); B01J 21/08 (2013.01); B01J 23/745 (2013.01); *C07C 2521/08* (2013.01); *C07C 2523/745* (2013.01)
(58) Field of Classification Search
    CPC ...... B01J 19/1893; B01J 21/08; B01J 23/745; B01J 29/48; C01B 3/50
    See application file for complete search history.

(56) References Cited

OTHER PUBLICATIONS

Borry, III, et al., "Structure and Density of Mo and Acid Sites in Mo-Exchanged H-ZSM5 Catalysts for Nonoxidative Methane Conversion," *J. Phys. Chem. B*, 1999, 103: pp. 5787-5796. (10 pages).
Brady et al., "Enhanced Methane Dehydroaromatization via Coupling with Chemical Looping," *ACS Catalysis*, May 2017, 7: pp. 3924-3928. (5 pages).
Bruijnincx et al., "Shale Gas Revolution: An Opportunity for the Production of Biobased Chemicals," *Angew. Chem. Int. Ed.*, 2013, 52: pp. 11980-11987. (8 pages).
Ding et al., "Methane Conversion to Aromatics on Mo/H-ZSM5: Structure of Molybdenum Species in Working Catalysts," *J. Phys. Chem. B*, 2001, 105: pp. 506-513. (8 pages).
Guo et al., "Direct, Nonoxidative Conversion of Methane to Ethylene, Aromatics, and Hydrogen," *Science*, May 2014, 344: pp. 616-619. (4 pages).
Gupta et al., "Heterogeneous Catalytic Conversion of Dry Syngas to Ethanol and Higher Alcohols on Cu-Based Catalysts," *ACS Catalysis*, Apr. 2011, 1: pp. 641-656. (16 pages).
Han et al., "Nonoxidative Direct Conversion of Methane on Silica-Based Iron Catalysts: Effect of Catalytic Surface," *ACS Catalysis*, 2019, 9: pp. 7984-7997. (14 pages).
Hao et al., "Enhanced Methane Conversion to Olefins and Aromatics by H-Donor Molecules under Nonoxidative Condition," *ACS Catalysis*, 2019, 9: pp. 9045-9050. (6 pages).
Horn et al., "Methane Activation by Heterogeneous Catalysis," *Catal. Lett.*, 2015, 145: p. 23-39 (17 pages).
Ismagilov et al., "Direct conversion of methane on Mo/ZSM-5 catalysts to produce benzene and hydrogen: achievements and perspectives," *Energy & Environmental Science*, 2008, 1: pp. 526-541. (16 pages).
Kosinov et al., "Selective Coke Combustion by Oxygen Pulsing During Mo/ZSM-5-Catalyzed Methane Dehydroaromatization," *Angew. Chem. Int. Ed.*, 2016, 55: pp. 15086-15090. (5 pages).
Li et al., "$SrCe_{0.7}Zr_{0.2}Eu_{0.1}O3$-based hydrogen transport water gas shift reactor," *International Journal of Hydrogen Energy*, 2012, 37: pp. 16006-16012. (7 pages).
Li et al., "High temperature $SrCe_{0.9}Eu_{0.1}O_{3-\delta}$ proton conducting membrane reactor for $H_2$ production using the water-gas shift reaction," *Applied Catalysis B: Environmental*, 2009, 92: pp. 234-239. (6 pages).
Li et al., "Hydrogen permeation through thin supported $SrCe_{0.7}Zr_{0.2}Eu_{0.2}O_{3-\delta}$ membranes; dependence of flux on defect equilibria and operating conditions," *Journal of Membrane Science*, 2011, 381: pp. 126-131. (6 pages).
Liu et al., "Catalytic Pyrolysis of Methane on Mo/H-ZSM5 with Continuous Hydrogen Removal by Permeation Through Dense Oxide Films," *Catalysis Letters*, Oct. 2002, 82(3-4): pp. 175-180. (6 pages).
Morejudo et al., "Direct conversion of methane to aromatics in a catalytic co-ionic membrane reactor," *Science*, Aug. 2016, 353(6299): pp. 563-566. (4 pages).

Natesakhawat et al., "Improved benzene production from methane dehydroaromatization over Mo/HZSM-5 catalysts via hydrogen-permselective palladium membrane reactors," *Catalysis Science & Technology*, 2015, 5: pp. 5023-5036. (14 pages).
Oh et al., "Effect of Eu dopant concentration in $SrCe_{1-x}Eu_xO_{3-\delta}$ on ambipolar conductivity," *Solid State Ionics*, 2009, 180: pp. 1233-1239. (7 pages).
Oh et al., "Hydrogen permeation through thin supported $SrZr_{0.2}Ce_{0.8-x}Eu_xO_{3-\delta}$ membranes," *Journal of Membrane Science*, 2009, 345: pp. 1-4. (4 pages).
Pakhare et al., "A review of dry ($CO_2$) reforming of methane over noble metal catalysts," *Chem. Soc. Rev.*, 2014, 43: pp. 7813-7837. (25 pages).
Rival et al., "Oxygen-Free Methane Aromatization in a Catalytic Membrane Reactor," *Ind. Eng. Chem. Res.*, 2001, 40: pp. 2212-2219. (8 pages).
Sakbodin et al., "Dual utilization of greenhouse gases to produce $C_{2+}$ hydrocarbons and syngas in a hydrogen-permeable membrane reactor," *Journal of Membrane Science*, Oct. 2019, 595: 117557. (6 pages).
Sakbodin et al., "Hydrogen-Permeable Tubular Membrane Reactor: Promoting Conversion and Product Selectivity for Non-Oxidative Activation of Methane over an Fe(c)$SiO_2$ Catalyst," *Agnew. Chem.*, 2016, 128: pp. 16383-16386. (4 pages).
Tonkovich et al., "Enhanced $C_2$ Yields from Methane Oxidative Coupling by Means of a Separative Chemical Reactor," *Science*, Oct. 1993, 262(5131): pp. 221-223. (3 pages).
Wang et al., "Characterization of a Mo/ZSM-5 Catalyst for the Conversion of Methane to Benzene," *Journal of Catalysis*, 1997, 169: pp. 347-358. (12 pages).
Wang et al., "Dehydrogenation and aromatization of methane under non-oxidizing conditions," *Catalysis Letters*, 1993, 21: pp. 35-41. (7 pages).
Wang et al., "Production of ultra highly pure $H_2$ and higher hydrocarbons from methane in one step at mild temperatures and development of the catalyst under non-equilibrium reaction conditions," *Chem. Commun.*, 2001, pp. 1952-1953. (2 pages).
Xue et al., "Gas to Liquids: Natural Gas Conversion to Aromatic Fuels and Chemicals in a Hydrogen-Permeable Ceramic Hollow Fiber Membrane Reactor," *ACS Catalysis*, Mar. 2016, 6: pp. 2448-2451. (4 pages).
Yoon et al., "Fabrication of Thin-Film $SrCe_{0.9}Eu_{0.1}O_{3-\delta}$ Hydrogen Separation Membranes on Ni—$SrCeO_3$ Porous Tubular Supports," *J. Am. Ceram. Soc.*, 2009, 92(8): pp. 1849-1852. (4 pages).
Alvarez-Galvan et al., "Direct methane conversion routes to chemicals and fuels," *Catalysis Today*, 2011, 171: pp. 15-23. (9 pages).
Borry, III, et al., "Non-oxidative catalytic conversion of methane with continuous hydrogen removal," *Natural Gas Conversion V, Studies in Surface Science and Catalysis*, 1998, 119: pp. 403-410. (8 pages).
Cao et al., "Natural Gas to Fuels and Chemicals: Improved Methane Aromatization in an Oxygen-Permeable Membrane Reactor," *Angew. Chem. Int. Ed.*, 2013, 52: pp. 13794-13797. (4 pages)
Cao et al., "Natural Gas to Fuels and Chemicals: Improved Methane Aromatization in an Oxygen-Permeable Membrane Reactor," *Angewandte Chemie*, 2013, 125(51): pp. 14039-14042. (4 pages).
Deangelis et al., "Sol-gel synthesis of nanocrystalline fayalite ($Fe_2SiO_4$)," *American Mineralogist*, 2012, 97: pp. 653-656. (4 pages).
Fabbri et al., "Materials challenges toward proton-conducting oxide fuel cells: a critical review," *Chemical Society Reviews*, 2010, 39: pp. 4355-4369. (15 pages).
Hickman et al., "Production of Syngas by Direct Catalytic Oxidation of Methane," *Science*, Jan. 1993, 259: pp. 343-346. (4 pages).
Iliuta et al., "Methane Nonoxidative Aromatization over Ru—Mo/HZSM-5 in a Membrane Catalytic Reactor," *Ind. Eng. Chem. Res.*, 2002, 41: pp. 2371-2378. (8 pages).
Keller et al., "Synthesis of Ethylene via Oxidative Coupling of Methane. I. Determination of Active Catalysts," *Journal of Catalysis*, 1982, 73: pp. 9-19. (11 pages).
Lee et al., "Oxidative coupling of methane to higher hydrocarbons," *Catalysis Reviews: Science and Engineering*, 1988, 30(2): pp. 249-280. (32 pages).

(56) References Cited

OTHER PUBLICATIONS

Li et al., "Design and optimization of catalysts and membrane reactors for the non-oxidative conversion of methane," *Chemical Engineering Science*, 2002, 57: pp. 4595-4604. (10 pages).

Ma et al., "Carbonaceous Deposition on Mo/HMCM-22 Catalysts for Methane Aromatization: A TP Technique Investigation," *Journal of Catalysis*, 2002, 208: pp. 260-269. (10 pages).

Ma et al., "On the Induction Period of Methane Aromatization over Mo-Based Catalysts," *Journal of Catalysis*, 2000, 194: pp. 105-114. (10 pages).

Ma et al., "Recent progress in methane dehydroaromatization: From laboratory curiosities to promising technology," *Journal of Energy Chemistry*, 2013, 22: pp. 1-20. (20 pages).

Oh et al., "Catalytic consequences of cation and anion substitutions on rate and mechanism of oxidative coupling of methane over hydroxyapatite catalysts," *Fuel*, 2017, 191: pp. 472-485. (14 pages).

Oh et al., "Direct Non-Oxidative Methane Conversion in a Millisecond Catalytic Wall Reactor," *Angew. Chem. Int. Ed.*, 2019, 58: pp. 7083-7086. (4 pages).

Oh et al., "Influences of cation and anion substitutions on oxidative coupling of methane over hydroxyapatite catalysts," *Fuel*, 2016, 167: pp. 208-217. (10 pages).

Spivey et al., "Catalytic aromatization of methane," *Chem. Soc. Rev.*, 2014, 43: pp. 792-803. (12 pages).

Sun et al., "Methane dehydroaromatization with periodic $CH_4$-$H_2$ switch: A promising process for aromatics and hydrogen," *Journal of Energy Chemistry*, 2015, 24: pp. 257-263. (7 pages).

Tessonnier et al., "Methane dehydro-aromatization on Mo/ZSM-5: About the hidden role of Brønsted acid sites," *Applied Catalysis A: General*, 2008, 336: pp. 79-88. (10 pages).

Wang et al., "Catalytic conversion of methane to benzene over Mo/ZSM-5," *Topics in Catalysis*, 1996, 3: pp. 289-297. (9 pages).

Wang et al., "Study on methane aromatization over $MoO_3$/HMCM-49 catalyst," *Catalysis Today*, 2004, 93-95: pp. 75-80. (6 pages).

Weckhuysen et al., "Conversion of Methane to Benzene over Transition Metal Ion ZSM-5 Zeolites. I. Catalytic Characterization," *Journal of Catalysis*, 1998, 175: pp. 338-346. (9 pages).

Wu et al., "The synthesis of Mo/H-MCM-36 catalyst and its catalytic behavior in methane non-oxidative aromatization," *Catalysis Communications*, 2005, 6: pp. 449-454. (6 pages).

Xu et al., "The catalytic stability of Mo/HZSM-5 in methane dehydroaromatization at severe and periodic $CH_4$-$H_2$ switch operating conditions," *Chemical Engineering Journal*, 2011, 168: pp. 390-402. (13 pages).

* cited by examiner

SYSTEMS, METHODS, AND DEVICES FOR METHANE CONVERSION VIA GAS RECYCLING

CROSS-REFERENCE TO RELATED APPLICATION(S)

The present application claims the benefit of U.S. Provisional Application No. 63/189,672, filed May 17, 2021, entitled "System, Devices, and Methods for Gas Conversion," which is incorporated by reference herein in its entirety.

STATEMENT REGARDING FEDERALLY SPONSORED RESEARCH

This invention was made with government support under CBET1264599 awarded by the National Science Foundation (NSF). The government has certain rights in the invention.

FIELD

The present disclosure relates generally to conversion of methane, and more particularly, to conversion of methane into liquid aromatics, for example, by direct non-oxidative methane conversion (DNMC).

BACKGROUND

Conversion of natural gas into liquid fuels can allow for easier and less expensive transport from remote extraction sites. In conventional systems, methane ($CH_4$), which is the main constituent of natural gas, can be converted to value-added hydrocarbons via the steam reforming of $CH_4$ to produce syngas ($CO+H_2$), followed by the Fischer-Trøpsch process; however, such systems result in low carbon and energy efficiencies. Other systems have employed direct conversion routes, such as oxidative coupling of methane (OCM) or direct non-oxidative methane conversion (DNMC). Compared with other approaches, DNMC can be more selective, given its unique capability in forming $C_2+$ hydrocarbons ($C_2$ hydrocarbons and aromatics) and $H_2$ while circumventing intermediate energy intensive step. In addition, DNMC can use methane as the only reactant, which can be beneficial for a modular unit at a remote extraction site. Yet, in conventional DNMC systems, the conversion can be hindered by thermodynamic limitations, as well as the high rate of catalyst deactivation from coke formation.

Embodiments of the disclosed subject matter may address one or more of the above-noted problems and disadvantages, among other things.

SUMMARY

Embodiments of the disclosed subject matter system provide systems, methods, and devices for methane conversion via gas recycling. In some embodiments, a first stage can provide direct non-oxidative methane conversion (DNMC) to convert at least some methane into $C_2$ hydrocarbons, hydrogen gas ($H_2$), and aromatics. An aromatics separation device, downstream of the first stage, can be used to separate (or remove) at least some of the produced aromatics, for example, by condensing the aromatics. A second stage, downstream of the aromatics separation device, can then be used to separate (or remove) at least some of the produced $H_2$ from the remaining methane, $C_2$ hydrocarbons, and aromatics, for example, by permeating hydrogen ions through a membrane. An output of the second stage can then be recycled back to the input of the first stage for reprocessing, for example, to convert additional methane and remove additional aromatics and $H_2$.

In some embodiments, the second stage can operate at a different temperature than the first stage, for example, to avoid formation of coke in the second stage that could otherwise impede $H_2$ removal via membrane permeation. In some embodiments, providing a stage for DNMC separate from the stage for $H_2$ separation can circumvent the thermodynamic limitations encountered by conventional DNMC (e.g., by operating at a higher temperature) and alleviate catalyst deactivation (e.g., by avoiding coke formation), while also producing high purity $H_2$ and improving aromatics liquid yield. In some embodiments, the second stage can be configured for autothermal operation, for example, by using the heat generated from a combustion reaction between separated $H_2$ (e.g., permeated through a membrane to a sweep gas volume) and oxygen (e.g., oxygen gas ($O_2$) or an oxygen-containing compound) in a sweep gas.

Alternatively, in some embodiments, the first stage comprises an integrated membrane reactor for performing DNMC and $H_2$ separation, and the second stage comprises another integrated membrane reactor for performing further DNMC and $H_2$ separation. For each of the integrated membrane reactors, a sweep gas comprising $O_2$ or an oxygen-containing compound can be flowed through a sweep gas volume on a permeate-side of the membrane opposite to the gas flow volume where methane is converted. Oxygen ions can back-diffuse from the permeate-side to the retentate-side of the membrane, where the oxygen reacts with carbon produced by the DNMC to prevent, or at least reduce, coking on the membrane. Moreover, each of the integrated membrane reactors can be configured for autothermal operation by using the heat generated from a combustion reaction between permeated $H_2$ and oxygen in the sweep gas.

In a representative embodiment, a methane conversion system can comprise first and second membrane reactors, first and second gas supplies, an aromatics separation device, and a recycle line. The first membrane reactor can comprise a first gas flow volume, a second gas flow volume, and a first membrane separating the first gas flow volume from the second gas flow volume. The first gas flow volume can have a first catalyst therein. The first gas supply can be coupled to the second gas flow volume and can be constructed to provide a first sweep gas to the second gas flow volume. The first sweep gas can comprise $O_2$ or an oxygen-containing compound. The aromatics separation device can be connected to receive a first processed stream from the first gas flow volume. The second membrane reactor can comprise a third gas flow volume, a fourth gas flow volume, and a second membrane separating the third gas flow volume from the fourth gas flow volume. The third gas flow volume can have a second catalyst therein. The second gas supply can be coupled to the fourth gas flow volume and can be constructed to provide a second sweep gas to the fourth gas flow volume. The second sweep gas can comprise $O_2$ or an oxygen-containing compound. The recycle line can comprise one or more fluid conduits. The first gas flow volume of the first membrane reactor can be connected to receive a recycle stream from the third gas flow volume of the second membrane reactor via the recycle line.

The first reactor can be constructed to convert at least some $CH_4$ in an input gas flow stream provided to the first gas flow volume of the first reactor, so as to provide a first processed stream and such that a quantity of $CH_4$ in the first processed stream is less than that in the input gas flow stream, the first processed stream comprising $CH_4$, $C_2$ hydrocarbons, and aromatics. The $C_2$ hydrocarbons are acetylene ($C_2H_2$), ethylene ($C_2H_4$), ethane ($C_2H_6$), or any combination of the foregoing, and the aromatics are benzene ($C_6H_6$), toluene ($C_7H_8$), naphthalene ($C_{10}H_8$), or any combination of the foregoing. The first membrane can be constructed such that at least some $H_2$ is removed from the first gas flow volume by hydrogen ions permeating through the first membrane into the second gas flow volume and such that oxygen ions permeate through the first membrane from the second gas flow volume into the first gas flow volume so as to reduce coking of the first membrane. The first reactor can be constructed for autothermal operation via an exothermic reaction between the permeated hydrogen in the second gas flow volume and the $O_2$ or oxygen-containing compound in the second gas flow volume.

The aromatics separation device can be constructed to remove at least some aromatics from the received first processed stream, so as to provide a second processed stream comprising $CH_4$ and $C_2$ hydrocarbons, and to provide a first output stream comprising the removed at least some aromatics. A quantity of the aromatics in the second processed stream can be less than in the first processed stream. The second reactor can be constructed to convert at least some $CH_4$ in the second processed stream provided to the third gas flow volume of the second reactor, so as to provide a recycle stream to the recycle line and such that a quantity of $CH_4$ in the recycle stream is less than in the second processed stream. The second processed stream can comprise $C_2$ hydrocarbons and aromatics. The second membrane can be constructed such that at least some $H_2$ is removed from the third gas flow volume by hydrogen ions permeating through the second membrane into the fourth gas flow volume and such that oxygen ions permeate through the second membrane from the fourth gas flow volume into the third gas flow volume so as to reduce coking of the second membrane. The second reactor can be constructed for autothermal operation via an exothermic reaction between the permeated hydrogen in the fourth gas flow volume and the $O_2$ or oxygen-containing compound in the fourth gas flow volume.

In a representative embodiment, a methane conversion system can comprise a first reactor, an aromatics separation device, a second reactor, and a recycle line. The first reactor can have an inlet and an outlet. The aromatics separation device can have an inlet, a first outlet, and a second outlet. The inlet of the separation device can be connected to receive a first processed stream from the outlet of the first reactor. The second reactor can have a first gas flow volume, a second gas flow volume, and a membrane separating the first gas flow volume from the second gas flow volume. The first gas flow volume can be connected to receive a second processed stream from the first outlet of the aromatics separation device. The recycle line can comprise one or more fluid conduits, and the inlet of the first reactor can be connected to receive a recycle stream from first gas flow volume via the recycle line.

The first reactor can be constructed to convert at least some $CH_4$ in an input gas flow stream provided to the inlet of the first reactor, so as to provide to the outlet of the first reactor the first processed stream and such that a quantity of $CH_4$ in the first processed stream is less than that in the input gas flow stream. The first processed stream can comprise $CH_4$, $C_2$ hydrocarbons, $H_2$, and aromatics. The aromatics separation device can be constructed to remove at least some aromatics from the first processed stream provided to the inlet of the aromatics separation device, so as to provide to the first outlet of the aromatics separation device a second processed stream comprising $CH_4$, $C_2$ hydrocarbons, and $H_2$, and to provide to the second outlet of the aromatics separation device a first output stream comprising the removed at least some aromatics. A quantity of the aromatics in the second processed stream can be less than in the first processed stream. The second reactor can be constructed to remove at least some $H_2$ from the second processed stream, which is provided to the first gas flow volume, into the second gas flow volume via the membrane, so as to provide to the recycle line a recycle stream comprising $CH_4$ and $C_2$ hydrocarbons. A quantity of the $H_2$ in the recycle stream can be less than that in the second processed stream.

In another representative embodiment, a method can comprise converting at least some $CH_4$ in an input gas flow stream into $C_2$ hydrocarbons, $H_2$, and aromatics, thereby providing a first processed stream comprising $CH_4$, $C_2$ hydrocarbons, $H_2$, and aromatics. A quantity of $CH_4$ in the first processed stream can be less than that in the input gas flow stream. The method can further comprise removing at least some aromatics from the first processed stream, thereby providing a first output stream comprising the removed at least some aromatics and a second processed stream comprising $CH_4$, $C_2$ hydrocarbons, and $H_2$. A quantity of the aromatics in the second processed stream can be less than that in the first processed stream. The method can also comprise removing at least some $H_2$ from the second processed stream, thereby providing a recycle stream comprising $CH_4$ and $C_2$ hydrocarbons. A quantity of the $H_2$ in the recycle stream can be less than that in the second processed stream. The method can further comprise providing the recycle stream as at least part of the input gas flow stream.

Any of the various innovations of this disclosure can be used in combination or separately. This summary is provided to introduce a selection of concepts in a simplified form that are further described below in the detailed description. This summary is not intended to identify key features or essential features of the claimed subject matter, nor is it intended to be used to limit the scope of the claimed subject matter. The foregoing and other objects, features, and advantages of the disclosed technology will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Embodiments will hereinafter be described with reference to the accompanying drawings, which have not necessarily been drawn to scale. Where applicable, some elements may be simplified or otherwise not illustrated in order to assist in the illustration and description of underlying features. Throughout the figures, like reference numerals denote like elements.

DETAILED DESCRIPTION

General Considerations

Figure 1A:
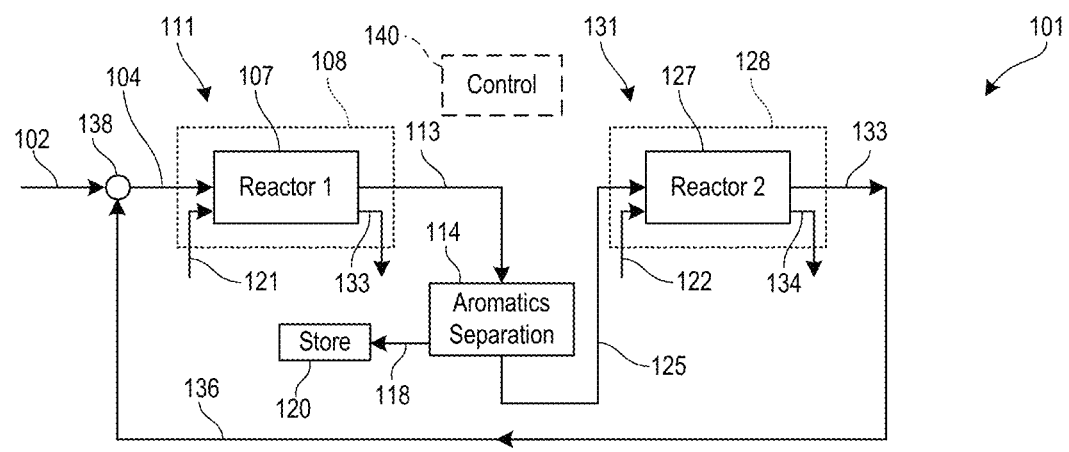
FIGS. 1A-1B are simplified schematic diagrams of exemplary methane conversion systems with gas recycling, according to one or more embodiments of the disclosed subject matter.

For purposes of this description, certain aspects, advantages, and novel features of the embodiments of this disclosure are described herein. The disclosed methods and systems should not be construed as being limiting in any way. Instead, the present disclosure is directed toward all novel and nonobvious features and aspects of the various disclosed embodiments, alone and in various combinations and sub-combinations with one another. The methods and systems are not limited to any specific aspect or feature or combination thereof, nor do the disclosed embodiments require that any one or more specific advantages be present, or problems be solved. The technologies from any embodiment or example can be combined with the technologies described in any one or more of the other embodiments or examples. In view of the many possible embodiments to which the principles of the disclosed technology may be applied, it should be recognized that the illustrated embodiments are exemplary only and should not be taken as limiting the scope of the disclosed technology.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one skilled in the art.

The disclosure of numerical ranges should be understood as referring to each discrete point within the range, inclusive of endpoints, unless otherwise noted. Unless otherwise indicated, all numbers expressing quantities of components, molecular weights, percentages, temperatures, times, and so forth, as used in the specification or claims are to be understood as being modified by the term "about." Accordingly, unless otherwise implicitly or explicitly indicated, or unless the context is properly understood by a person skilled in the art to have a more definitive construction, the numerical parameters set forth are approximations that may depend on the desired properties sought and/or limits of detection under standard test conditions/methods, as known to those skilled in the art. When directly and explicitly distinguishing embodiments from discussed prior art, the embodiment numbers are not approximates unless the word "about" is recited. Whenever "substantially," "approximately," "about," or similar language is explicitly used in combination with a specific value, variations up to and including 10% of that value are intended, unless explicitly stated otherwise.

Directions and other relative references may be used to facilitate discussion of the drawings and principles herein but are not intended to be limiting. For example, certain terms may be used such as "inner," "outer,", "upper," "lower," "top," "bottom," "interior," "exterior," "left," right," "front," "back," "rear," and the like. Such terms are used, where applicable, to provide some clarity of description when dealing with relative relationships, particularly with respect to the illustrated embodiments. Such terms are not, however, intended to imply absolute relationships, positions, and/or orientations. For example, with respect to an object, an "upper" part can become a "lower" part simply by turning the object over. Nevertheless, it is still the same part, and the object remains the same.

As used herein, "comprising" means "including," and the singular forms "a" or "an" or "the" include plural references unless the context clearly dictates otherwise. The term "or" refers to a single element of stated alternative elements or a combination of two or more elements unless the context clearly indicates otherwise.

Although there are alternatives for various components, parameters, operating conditions, etc. set forth herein, that does not mean that those alternatives are necessarily equivalent and/or perform equally well. Nor does it mean that the alternatives are listed in a preferred order, unless stated otherwise. Unless stated otherwise, any of the groups defined below can be substituted or unsubstituted.

Unless explained otherwise, all technical and scientific terms used herein have the same meaning as commonly understood to one skilled in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Features of the presently disclosed subject matter will be apparent from the following detailed description and the appended claims.

Overview of Terms

The following is provided to facilitate the description of various aspects of the disclosed subject matter and to guide those skilled in the art in the practice of the disclosed subject matter.

$C_2$ hydrocarbons: Compounds formed by the conversion of methane ($CH_4$) and including two carbons ($C_2$) and at least two hydrogens ($H_2$). In some embodiments, the $C_2$ hydrocarbons can include acetylene ($C_2H_2$), ethylene ($C_2H_4$), ethane ($C_2H_6$), or combinations thereof. In some embodiments, the predominant $C_2$ hydrocarbon formed by the conversion of methane is ethylene.

Aromatics: Hydrocarbons formed by the conversion of methane and larger/heavier than the $C_2$ hydrocarbons. In some embodiments, the aromatics can include benzene ($C_6H_6$), toluene ($C_7H_8$), naphthalene ($C_{10}H_8$), or combinations thereof.

Fe@SiO$_2$: A catalyst formed of iron (Fe) and silica ($SiO_2$), where @ denotes confinement, and characterized by lattice-confined single iron sites embedded within a silica matrix.

Autothermal operation: Operation of the system where the heat used to drive one reaction (e.g., a direct non-oxidative methane conversion (DNMC)) or operation (e.g., hydrogen permeation) is provided by a simultaneous (or substantially simultaneous) exothermic reaction. In some embodiments, the exothermic reaction comprises combustion of hydrogen and oxygen to form water, where the hydrogen is provided by permeation of hydrogen ions through a membrane.

Oxygen-containing compound: A compound having at least one atom of oxygen and capable of releasing the oxygen to react with hydrogen (e.g., to form water). In some embodiments, the oxygen-containing compound can comprise $CO_2$, $H_2O$, alcohols (e.g., methanol, ethanol, isopropanol, etc.).

Introduction

Direct non-oxidative methane conversion (DNMC) can be used to convert methane ($CH_4$) (e.g., in natural gas) into liquid aromatics, which may be easier to transport than $CH_4$ gas. In conventional systems, DNMC is constrained by low $CH_4$ conversion and thus low aromatics product yield due to thermodynamic limitations. In one or more embodiments of the disclosed subject matter, a gas-recycle system is provided with a first stage (e.g., a methane conversion reactor) and a separate second stage (e.g., a hydrogen ($H_2$) membrane separator) to achieve high $CH_4$ conversion (e.g., at least 40% after multiple cycles) and high aromatics yield (e.g., at least 50% after multiple cycles and/or with a product selectivity toward aromatics of at least 90%) by circumventing the thermodynamic limitations.

For example, in some embodiments, the methane conversion stage (e.g., first stage) can perform DNMC over a catalyst (e.g., Fe@SiO$_2$) in a packed reactor to produce $C_2$ products and aromatics, along with reaction product $H_2$. In some embodiments, the produced aromatics can then be removed, for example, by passing the product stream through a condenser. In some embodiments, the produced $H_2$ can also be removed, for example, by passing through an $H_2$-permeable membrane separator (e.g., a second stage). The unreacted $CH_4$, $C_2$ hydrocarbons, residual aromatics (if any), and residual $H_2$ (if any) in the product stream can then be sent back to the methane conversion stage via a recycle loop, for example, for the next round of DNMC reaction, aromatics removal, and $H_2$ removal.

In some embodiments, system performance can be further improved by employing an autothermal reactor configuration for the first stage, the second stage, or both. When provided as part of the first stage, the DNMC reaction can be performed over a catalyst (e.g., Fe@SiO$_2$) in a membrane reactor to produce C$_2$ hydrocarbons, aromatics, and H$_2$ gas in a products volume (e.g., a first gas flow volume). The membrane reactor can have an H$_2$-permeable membrane that separates the products volume from a sweep gas volume (e.g., a second gas flow volume), and a sweep gas can be flowed through the sweep gas volume. In some embodiments, the sweep gas can comprise oxygen gas (O$_2$) (e.g., air or a mixture of O$_2$ and with one or more other gases, such as He gas) or an oxygen-containing compound. Within the sweep gas volume, the permeated H$_2$ can react with the oxygen in the sweep gas to produce heat for the endothermic DNMC within the products volume (e.g., at least some of the heat required for the endothermic DNMC reaction, and preferably all of the heat required). In some embodiments, the membrane can allow for back diffusion of O$_2$ (e.g., via permeation of oxygen ions) from the sweep gas volume to the products volume, thereby oxidizing carbon species therein into carbon monoxide (CO) and thus reducing carbon deposition in the membrane reactor.

When provided as part of the second stage, the H$_2$ removal can be performed in a membrane reactor with an H$_2$-permeable membrane that separate a processed flow volume (e.g., a first gas flow volume) from a sweep gas volume (e.g., a second gas flow volume). A sweep gas can be flowed through the sweep gas volume. In some embodiments, the sweep gas can comprise oxygen gas (O$_2$) (e.g., air or a mixture of O$_2$ and with one or more other gases, such as He gas) or an oxygen-containing compound. Within the sweep gas volume, the permeated H$_2$ can react with the oxygen in the sweep gas to produce heat that maintains or raises a temperature of the membrane reactor (e.g., to support H$_2$ permeation through the membrane).

In an exemplary embodiment, each of the first and second stages employs an integrated membrane reactor with respective catalyst, and by using a sweep gas comprising O$_2$ or an oxygen-containing compound for each reactor. For each membrane reactor, the DNMC reaction can be performed over a catalyst (e.g., Fe@SiO$_2$) in a membrane reactor to produce C$_2$ hydrocarbons, aromatics, and H$_2$ gas in a products volume (e.g., a first gas flow volume). The membrane reactor can have an H$_2$-permeable membrane that separates the products volume from a sweep gas volume (e.g., a second gas flow volume). Within the sweep gas volume, the permeated H$_2$ can react with the oxygen in the sweep gas to produce heat for the endothermic DNMC within the products volume (e.g., at least some of the heat required for the endothermic DNMC reaction, and preferably all of the heat required). In some embodiments, the membrane can allow for back diffusion of O$_2$ (e.g., via permeation of oxygen ions) from the sweep gas volume to the products volume, thereby oxidizing carbon species therein into carbon monoxide (CO) and thus reducing carbon deposition in the membrane reactor. This can allow the reactors of the first and second stages to operate at a higher temperature (e.g., the same temperature for both stages) for greater hydrogen permeation and higher aromatic yield, while avoiding, or at least reducing, membrane coking.

Exemplary Methane Conversion System Configurations

FIG. 1A shows an exemplary gas recycle system 101 for methane conversion. In the illustrated example, the gas recycle system 101 includes a first stage 111, a second stage 131, an aromatics separation device 114 arranged inline between the first and second stages, and a recycle line 136 for returning a processed stream back to the first stage 111 for further processing. The first stage 111 can include a first integrated membrane reactor 107 configured for methane conversion (e.g., via DNMC) and hydrogen separation (e.g., by removing H$_2$ from a processed stream), and the second stage 130 can include a second integrated membrane reactor 127 configured for methane conversion and hydrogen separation. The recycling of a processed stream for further processing by the system can further improve process efficiency (e.g., by increasing the amount CH$_4$ converted and/or the amount of aromatics produced).

In the illustrated example, an initial methane feed 102 is provided via feed coupler 138 as an input gas flow stream 104 to the first membrane reactor 107 for conversion. For example, the first membrane reactor 107 can convert at least some methane in the input gas flow stream 104 to C$_2$ hydrocarbons, hydrogen gas (H$_2$), and aromatics. In addition, the first membrane reactor 107 can remove at least some of the produced H$_2$ by transport across (e.g., permeation through) a membrane. The resulting first processed stream 113 can thus include at least C$_2$ hydrocarbons and aromatics, as well as any unreacted methane and potentially hydrogen not removed through the membrane, where the quantity of methane in the first processed stream 113 is less than the initial quantity of methane in the input gas flow stream 104.

In some embodiments, the first membrane reactor 107 can be an H$_2$-permeable membrane reactor, for example, according to the reactor configurations or constructions described in U.S. Pat. No. 10,525,407, issued Jan. 7, 2020, and entitled "Systems, Methods, and Devices for Direct Conversion of Methane," which is incorporated by reference herein in its entirety. For example, the first membrane reactor 107 can comprise and/or define a first flow volume and a second flow volume, where the permeable membrane separates the first flow volume from the second flow volume. The first flow volume can receive the input gas flow stream 104, and the first processed stream 113 can be directed from an outlet (or outlet end) of the first flow volume.

A catalyst can be provided in the first flow volume of the first membrane reactor 107. In one or more embodiments, the catalyst can comprise metal elements doped (i.e., lattice doping) in the lattice of amorphous-molten-state materials made from Si bonded with one or two of elemental C, N or O, for example, SiO$_2$. In lattice doping, the dopant metal elements exchange with the lattice elements in the doped materials such that the metal dopant elements are confined in the lattice of the doped materials. For example, the amount of dopant metal can be between 0.001 wt % and 10 wt % of the total weight of the catalyst. For example, the dopant metal elements can be one or more of Li, Na, K, Mg, Al, Ca, Sr, Ba, Y, La, Ti, Zr, Ce, Cr, Mo, W, Re, Fe, Co, Ni, Cu, Zn, Ge, In, Sn, Pb, Bi, Mn, such as Fe. For example, the catalyst can comprise Fe@SiO$_2$, which has lattice-confined single iron sites embedded in the silica matrix. The Fe@SiO$_2$ catalyst disclosed herein can be formed according to the fabrication method described in U.S. Pat. No. 10,525,407, incorporated by reference above. Although the discussion above is directed to the Fe@SiO$_2$ catalyst, embodiments of the disclosed subject matter are not limited thereto. Rather, according to one or more contemplated embodiments, other catalysts may be used, such as but not limited to molybdenum/Zeolite Socony Mobil-5 (Mo/ZSM-5) or a noble metal.

The first reactor 107 can be provided in a first heating module 108, which heats and/or maintains the reactor 107 at a first temperature. The first heating module 108 can comprise a heater, a furnace, or both; however, alternative heating methodologies and configurations are also possible according to one or more contemplated embodiments. For example, instead of or in supplement to a heater of the first heating module 108, heat can be generated via an exothermic reaction between gas constituents in the first reactor 107, such as between a sweep gas and permeated hydrogen. In particular, a sweep gas comprising $O_2$ or an oxygen-containing compound can be provided on a permeate-side of the membrane. The permeated hydrogen can react with the oxygen to generate heat for the methane conversion in the first reactor 107.

Moreover, oxygen ions can back-diffuse through the membrane (e.g., from the permeate-side into the product volume) to oxidize carbon species produced by the methane conversion (e.g., forming CO), thereby avoiding, or at least reducing, coking of the membrane. The resulting first processed stream 113 may thus further include CO. By avoiding coking, the first reactor 107 can operate at a higher temperature, thereby offering greater hydrogen permeation and higher aromatic yields (e.g., ≥1100 K, as suggested by FIGS. 13A-13B).

The first processed stream 113 can be directed to an aromatics separation device 114, which can be configured to remove at least some of the aromatics from the first processed stream 112. For example, the aromatics separation device 114 can comprise a condenser that condenses the aromatics in the first processed stream 113 while retaining the remaining components (e.g., $CH_4$, $C_2$ hydrocarbons, CO, and $H_2$) in gaseous state to form a second processed stream 125. In some embodiments, the aromatics separation device 114 can include other components for pre-processing, such as a heat exchanger, chiller, etc., and/or other components for post-processing of removed aromatics, such as a distillation system, etc. The aromatics separation device 114 can be other than a condenser and/or employ separation techniques other than selective condensation according to one or more contemplated embodiments. In the illustrated example, the liquid aromatics can then be collected as a first output stream 118 for storage, transport, or use by module 120. For example, module 120 can comprise a storage container or a conduit for conveying liquid aromatics to a storage or for subsequent use. Alternatively, in some embodiments, module 120 can be omitted in favor of on-site use of the liquid aromatics.

The second processed stream 125 from the aromatics separation device 114 can include at least $C_2$ hydrocarbons, and as well as any unreacted methane and potentially hydrogen not removed by the first reactor 107 and/or aromatics not removed by the separation device 114, where the quantity of aromatics in the second processed stream 125 is less than the initial quantity of aromatics in the first processed stream 112. In the illustrated example, the second processed stream 125 is directed to the second reactor 127 for further methane conversion. For example, the second membrane reactor 127 can convert at least some methane in the second processed stream 125 to $C_2$ hydrocarbons, $H_2$, and aromatics. In addition, the second membrane reactor 127 can remove at least some of the produced $H_2$ by transport across (e.g., permeation through) a membrane. The resulting recycle stream 133 can thus include at least $C_2$ hydrocarbons and aromatics, as well as any unreacted methane and potentially hydrogen not removed through the membrane and/or CO, where the quantity of methane in the recycle stream 133 is less than the initial quantity of methane in the second processed stream 125.

In some embodiments, the second membrane reactor 127 can be an $H_2$-permeable membrane reactor, for example, according to the reactor configurations or constructions described in U.S. Pat. No. 10,525,407, incorporated by reference above. For example, the second membrane reactor 127 can comprise and/or define a third flow volume and a fourth flow volume, where the permeable membrane separates the third flow volume from the fourth flow volume. The third flow volume can receive the second processed stream 125, and the recycle stream 133 can be directed from an outlet (or outlet end) of the third flow volume. A catalyst can be provided in the third flow volume of the second membrane reactor 127. For example, the catalyst can be the same or different than the catalyst of the first membrane reactor 107.

The second reactor 127 can be provided in a second heating module 128, which heats and/or maintains the reactor 127 at a second temperature. The second heating module 128 can comprise a heater, a furnace, or both; however, alternative heating methodologies and configurations are also possible according to one or more contemplated embodiments. For example, instead of or in supplement to a heater of the second heating module 128, heat can be generated via an exothermic reaction between gas constituents in the second reactor 127, such as between a sweep gas and permeated hydrogen. In particular, a sweep gas comprising $O_2$ or an oxygen-containing compound can be provided on a permeate-side of the membrane. The permeated hydrogen can react with the oxygen to generate heat for the further methane conversion in the second reactor 127.

Moreover, oxygen ions can back-diffuse through the membrane (e.g., from the permeate-side into the product volume) to oxidize carbon species produced by the methane conversion (e.g., forming CO), thereby avoiding, or at least reducing, coking of the membrane. The resulting recycle stream 133 may thus further include CO. By avoiding coking, the second reactor 127 can operate at a higher temperature (e.g., a same temperature as the first reactor 107), thereby offering greater hydrogen permeation and higher aromatic yields (e.g., ≥1100 K, as suggested by FIGS. 13A-13B).

As noted above, the sweep gas for the first reactor 107 or the second reactor 127 can comprise $O_2$ (e.g., air, $O_2$ gas alone, or $O_2$ gas combined with one or more other gases) and/or an oxygen-containing compound (e.g., $CO_2$, $H_2O$, and/or alcohol), for example, to combust with permeated $H_2$ to provide heat supporting the methane conversion in the respective reactor. In the illustrated example, the sweep gas is provided to the second flow volume of the first reactor 107 via a sweep gas inlet feed 121, and a second outlet stream 133 can be directed from an outlet (or outlet end) of the second flow volume of the first reactor. In addition, the sweep gas is provided to the fourth flow volume of the second reactor 127 via a sweep gas inlet feed 122, and a third outlet stream 134 can be directed from an outlet (or outlet end of the fourth flow volume of the second reactor. The second outlet stream 133 and the third outlet stream 134 can each contain water, for example, resulting from the combustion between oxygen in the sweep gas and the permeated $H_2$. In some embodiments, the second and third outlet streams 133, 134 can be subjected to further processing (e.g., isolation of the $H_2$ and/or water from the sweep gas), storage, and/or use.

In the illustrated example, the recycle stream 133 can be returned to the inlet of the system 100 via recycle line 136, for re-processing in a next cycle, which can further convert additional methane that was unreacted in the previous cycle.

For example, the recycle line 136 can connect between an outlet of the second reactor 127 and a feed coupler 138. In some embodiments, the feed coupler 138 can combine the recycle stream 133 from the recycle line 136 with fresh methane from feed 102 for processing as input gas flow stream 104. Alternatively or additionally, in some embodiments, the feed coupler 138 can select between the recycle stream 133 from the recycle line 136 and the methane feed 102 for use as the input gas flow stream 104. For example, the recycle stream 133 can be used as the input gas flow stream 104 for repeated cycles (e.g., 3-10 passes through the first stage 111, aromatics separation device 114, and the second stage 131) until a majority (e.g., — 50%), most (e.g., —70%), or substantially all (e.g., —90% or more) of an initial methane batch has been converted, after which the feed coupler 138 can be switched to provide a new batch of methane from methane feed 102.

System 100 can further include a controller 140 operatively coupled to one, some, or all of the illustrated components and configured to control operation thereof. For example, the controller 140 can modify flow rates, feed gas composition, sweep gas composition, and/or temperature to regulate methane conversion efficiency and/or product selectivity. Gas flow lines within system 100 can include respective gas flow control and sensing module, which may include, for example, valves, temperature sensors, temperature controllers, pumps, mass flow controllers, and/or other devices to monitor and/or control the variables of gas flow rates, reaction temperatures, and/or feed and sweep gas compositions to optimize or otherwise control methane conversion product formation, as described herein. In some embodiments, the controller 140 can also control operation of components not illustrated, such as pumps, valves, switches, etc., to effect flow of fluid (e.g., liquid or gas mixtures) through the system.

Figure 1B:
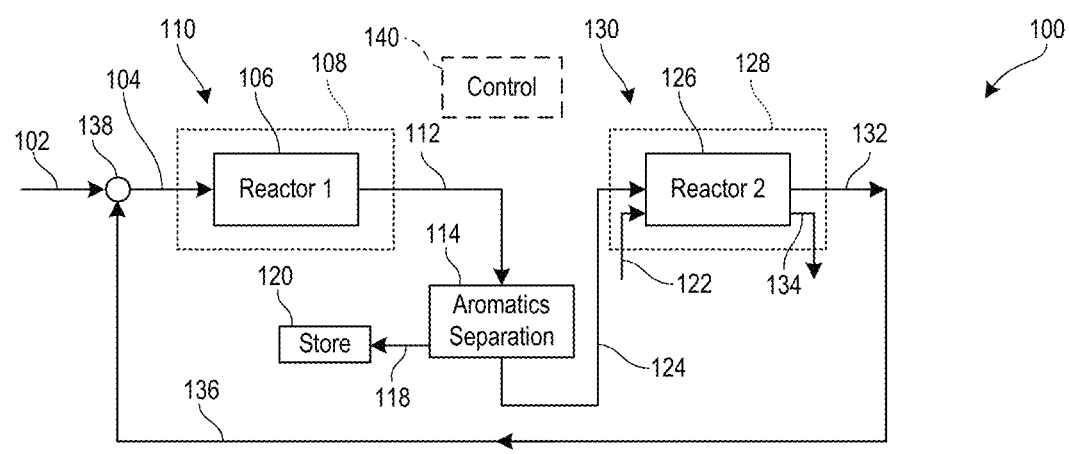

Alternatively, in some embodiments, methane conversion and hydrogen separation can be provided in separate stages rather than performed within the same reactor. For example, FIG. 1B shows an exemplary gas recycle system 100 for methane conversion. In the illustrated example, the gas recycle system 100 includes a first stage 110, a second stage 130, an aromatics separation device 114 arranged inline between the first and second stages, and a recycle line 136 for returning a processed stream back to the first stage 110 for further processing. In some embodiments, the first stage 110 can include a first reactor 106 configured for methane conversion (e.g., via DNMC), and the second stage 130 can include a second reactor 126 configured for hydrogen separation (e.g., by removing $H_2$ from a processed stream). For example, the first reactor 106 can be a fixed-bed reactor (e.g., with Fe@$SiO_2$ catalyst, Mo/ZSM-5 catalyst, noble metal catalyst, or any other catalyst) and the second reactor 126 can be a $H_2$-permeable membrane separator.

The first reactor 106 can convert at least some methane in the input gas flow stream 104 to $C_2$ hydrocarbons, hydrogen gas ($H_2$), and aromatics. The resulting first processed stream 112 can thus include at least $C_2$ hydrocarbons, $H_2$, and aromatics, as well as any unreacted methane, where the quantity of methane in the first processed stream 112 is less than the initial quantity of methane in the input gas flow stream 104. The first processed stream 112 can be directed to an aromatics separation device 114, which can be configured to remove at least some of the aromatics from the first processed stream 112. For example, the aromatics separation device 114 can comprise a condenser that condenses the aromatics in the first processed stream 112 while retaining the remaining components (e.g., $CH_4$, $C_2$ hydrocarbons, and $H_2$) in gaseous state to form a second processed stream 124.

The second processed stream 124 from the aromatics separation device 114 can include at least $C_2$ hydrocarbons and $H_2$, and as well as any unreacted methane and potentially aromatics not removed by the separation device 114, where the quantity of aromatics in the second processed stream 124 is less than the initial quantity of aromatics in the first processed stream 112. In the illustrated example of FIG. 1B, the second processed stream 124 is directed to the second reactor 126 for hydrogen separation (also referred to herein as hydrogen removal or hydrogen isolation). The resulting product stream 132 can thus include at least $C_2$ hydrocarbons, as well as unreacted methane and potentially aromatics not removed by the separation device 114 and $H_2$ not removed by the second reactor 126, where the quantity of $H_2$ in the product stream 132 is less than the initial quantity of $H_2$ in the second processed stream 124. Similar to FIG. 1A, the product stream 132 in FIG. 1B can be returned to the inlet of the system 100 via recycle line 136 for re-processing in a next cycle, which can further convert additional methane that was unreacted in the previous cycle.

By decoupling the methane conversion reaction from the hydrogen removal, the processes can be separately optimized, for example, to operate at respective temperatures that increase process efficiency (e.g., enhancing $CH_4$ conversion and/or aromatics yield) and/or maintain system operability (e.g., by avoiding coke formation). Depending on the catalyst employed in the first reactor 106, the first reactor 106 can operate at a different temperature (e.g., higher when using Fe@$SiO_2$ or lower when using Mo/ZSM-5) than the second reactor 126. For example, the first temperature can be at least 1000 K (e.g., ≥1200 K) for Fe@$SiO_2$ catalyst, and the second temperature can be less than or equal to 1100 K (e.g., ≤800 K).

Figure 1C:
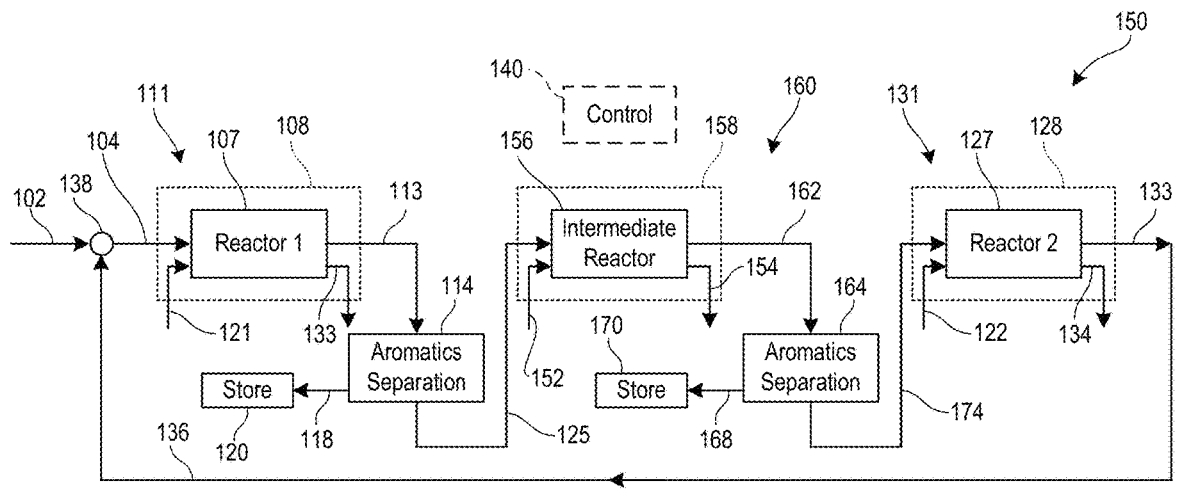
FIG. 1C is a simplified schematic diagram of another methane conversion system with multiple aromatic separation stages, according to one or more embodiments of the disclosed subject matter.

Although only two stages are illustrated in FIGS. 1A-1B, embodiments of the disclosed subject matter are not limited thereto. Rather, in some embodiments, one or more intermediate reaction stages (with or without associated aromatics separation devices) can be provided between an initial methane conversion stage (e.g., first stage 110 or 111) and a final methane conversion stage (e.g., second stage 131) or a final $H_2$-separation stage (e.g., second stage 130) to provide further processing (e.g., additional conversion of methane and/or removal of aromatics prior to hydrogen removal and recycling). For example, FIG. 1C shows another gas recycle system 150 for methane conversion, where an intermediate stage 160 for further processing is provided inline after the aromatics separation device 114 and before second stage 131. The second processed stream 125 from the aromatics separation device 114 is provided to the intermediate reactor 156 of the intermediate stage 160.

In some embodiments, the intermediate reactor 156 can function similar to the first reactor 107, for example, to provide an additional stage of methane conversion and hydrogen separation. Alternatively, in some embodiments, the intermediate reactor 156 can function similar to the second reactor 127, for example, to provide an additional stage of methane conversion and hydrogen separation or similar to second reactor 126, for example, to provide an additional stage of hydrogen separation without associated methane conversion. The intermediate reactor 156 can be provided in a third heating module 158, which heats and/or maintains the reactor 156 at a third temperature. Depending on system operation, the third temperature may be the same as the first temperature (e.g., when providing additional DNMC) or different than the first temperature (e.g., to provide improved hydrogen separation at higher temperatures). For example, the intermediate reactor 156 can have a membrane that separates a product flow volume from a sweep gas flow volume. The second processed stream 124 can be provided to the product flow volume of the intermediate reactor 156 and can exit therefrom as intermediate processed stream 162. A sweep gas inlet feed 152 (e.g., similar to sweep gas inlet feed 122) can be provided to the sweep gas flow volume of the intermediate reactor 156 and can exit therefrom as outlet stream 154 (e.g., similar to outlet stream 134).

In the illustrated example, the intermediate processed stream 162 is directed to a second aromatics separation device 164 (e.g., similar to aromatics separation device 114), which can be configured to remove at least some of the aromatics from the intermediate processed stream 162. For example, the aromatics separation device 164 can comprise a condenser that condenses the aromatics in the intermediate processed stream 162 while retaining the remaining components (e.g., $CH_4$, $C_2$ hydrocarbons, and $H_2$) in gaseous state to form further processed stream 174, which can then be directed to the second reactor 126. In the illustrated example, the liquid aromatics can then be collected as a second output stream 168 (e.g., similar to output stream 118) for storage, transport, or use by module 170 (e.g., similar to module 120). Although shown separately in FIG. 1C, in some embodiments, modules 120, 170 can be combined, for example, as a single volume within a container, flow volumes connecting a common conduit, separate volumes within a common structure, or any other configuration.

Figure 1D:
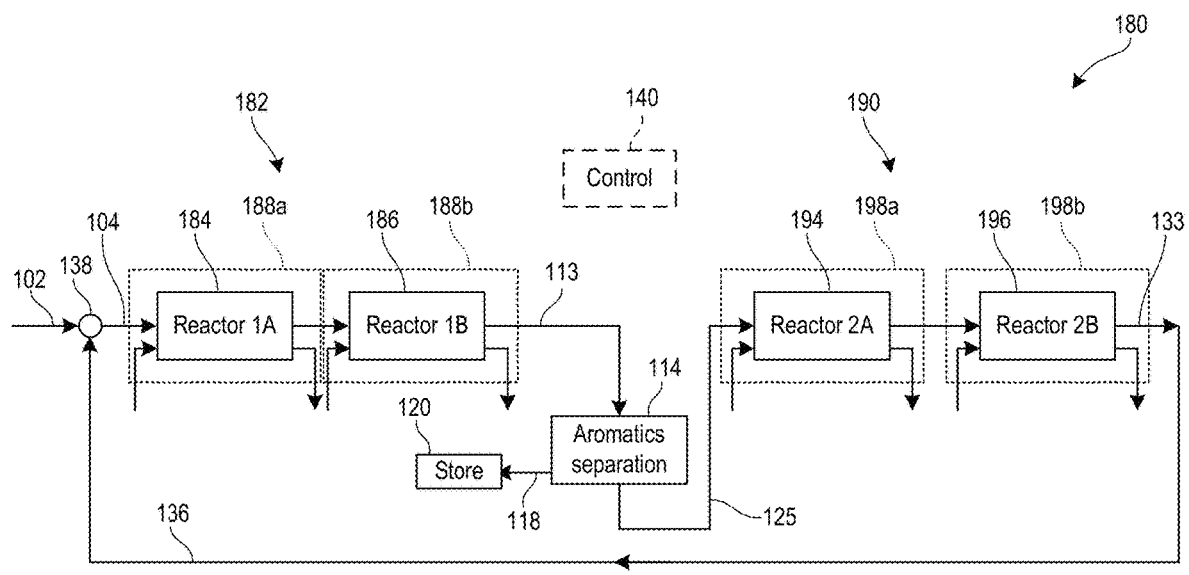
FIG. 1D is a simplified schematic diagram of another methane conversion system with multiple reactor stages, according to one or more embodiments of the disclosed subject matter.

Although FIGS. 1A-1C illustrate only a single reactor in each stage, embodiments of the disclosed subject matter are not limited thereto. Rather, in some embodiments, a stage can include multiple reactors. For example, FIG. 1D shows another gas recycle system 180 for methane conversion, where a first stage 182 (e.g., for methane conversion via DNMC) includes multiple first reactors 184, 186 and a second stage 190 (e.g., for methane conversion via DNMC or for $H_2$ separation) includes multiple second reactors 194, 196. The first processed stream 113 output from the ultimate first reactor 186 of the first stage 182 can be directed to aromatics separation device 114, and the second processed stream 125 from the aromatics separation device 114 can be directed to the initial second reactor 194 of the second stage 190.

In some embodiments, the first reactors 184, 186 can have similar structures and/or operate similarly to each other, for example, each similar to reactor 107 of FIG. 1A or reactor 106 of FIG. 1B. Alternatively or additionally, the first reactors 184, 186 can have different structures (e.g., one fixed-bed and the other a permeable membrane reactor). Each first reactor 184, 186 can be provided in a respective heating module 188a, 188b (e.g., similar to heating module 108), which heat and/or maintain the respective reactor at a respective temperature. In some embodiments, the first reactors 184, 186 can operate at a same temperature (e.g., at least 1000 K). Alternatively, in some embodiments, the reactors 184, 186 can operate at different temperatures. Although shown separately in FIG. 1D, in some embodiments, heating modules 188a, 188b can be combined together in a single module, for example, when first reactors 184, 186 operate at the same temperature. Moreover, although only two reactors are illustrated for first stage 182, any number of reactors can be provided in series and/or in parallel.

In some embodiments, the second reactors 194, 196 can have similar structures and/or operate similarly to each other, for example, each similar to reactor 127 of FIG. 1A or reactor 126 of FIG. 1B. Alternatively or additionally, the second reactors 194, 196 can have different structures, for example, one as a permeable membrane separator (e.g., no catalyst) and the other as a permeable membrane reactor (e.g., with catalyst). Similar to reactor 127 in FIG. 1A, reactor 194 can be provided with a sweep gas inlet feed, and reactor 196 can be provided with a sweep gas inlet feed 192b. In some embodiments, a composition of the sweep gas provided to each reactor 194, 196 can be the same. Alternatively, in some embodiments, the sweep gas composition of the inlet feed for reactor 194 can be different from the sweep gas composition of the inlet feed for reactor 196, for example, depending on the operation and/or configuration of the corresponding second reactor.

Each second reactor 194, 196 can be provided in a respective heating module 198a, 198b (e.g., similar to heating module 128), which heat and/or maintain the respective reactor at a respective temperature. In some embodiments, the second reactors 194, 196 can operate at a same temperature (e.g., less than 1000 K). Alternatively, in some embodiments, the reactors 194, 196 can operate at different temperatures. Although shown separately in FIG. 1D, in some embodiments, heating modules 198a, 198b can be combined together in a single module, for example, when second reactors 194, 196 operate at the same temperature. Moreover, although only two reactors are illustrated for stage 190, any number of reactors can be provided in series and/or in parallel.

Exemplary Reactor Configurations

Figure 2A:
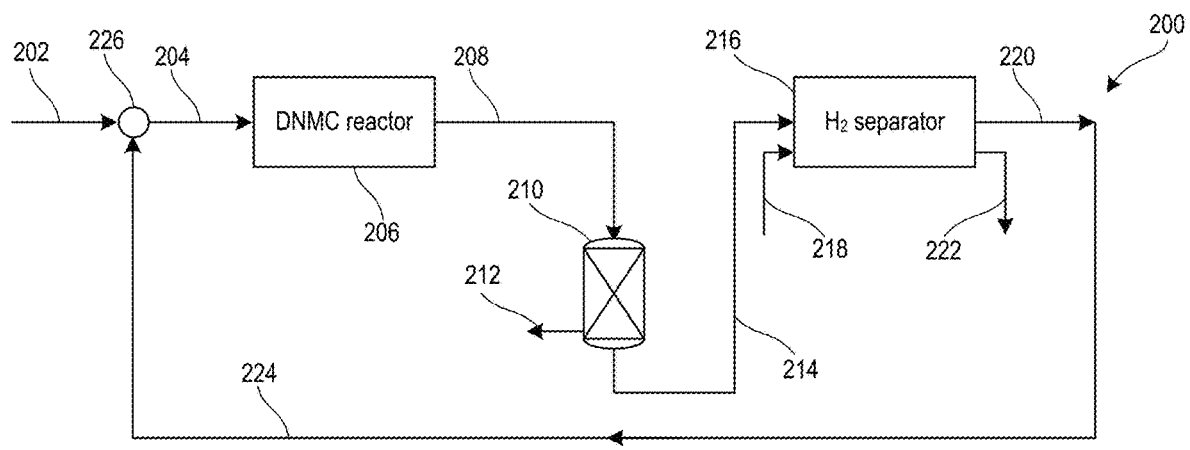
FIG. 2A is a simplified schematic diagram of another methane conversion system, according to one or more embodiments of the disclosed subject matter.
Figure 2B:
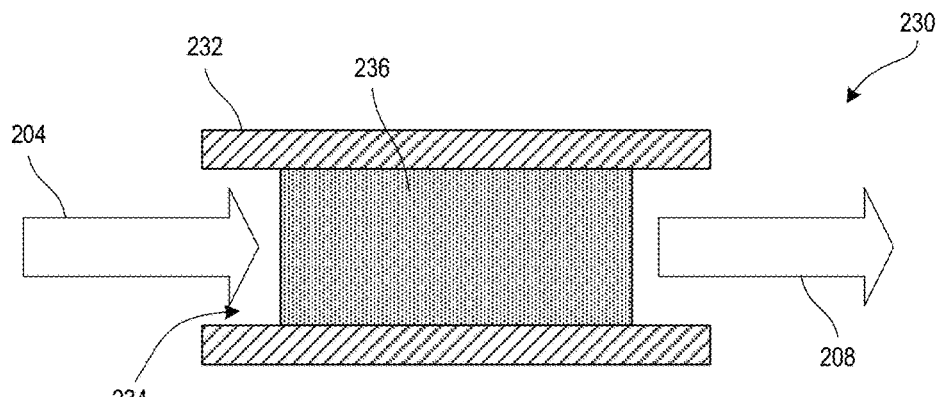
FIG. 2B is a simplified cross-sectional view of an exemplary fixed-bed reactor setup that can be used for the direct non-oxidative methane conversion (DNMC) reactor of FIG. 2A, according to one or more embodiments of the disclosed subject matter.

FIG. 2A, shows a schematic of a gas recycle system 200 with a recycle loop. Methane from an initial methane feed 202 can be provided as an input gas flow stream 204 to DNMC reactor 206 via feed coupler 226. The DNMC reactor 206 can include a catalyst for performing DNMC at high temperature, thereby producing a first processed flow stream 208 comprising equilibrated gas mixtures of $CH_4$, $H_2$, $C_2$ products, and aromatics in a single step. In some embodiments, the DNMC reactor 206 can be a fixed-bed reactor or an $H_2$-permeable membrane reactor. For example, FIG. 2B illustrates a fixed-bed reactor setup 230 that can be used for the DNMC reactor 206 of FIG. 2A. The fixed-bed reactor setup 230 can include a reactor housing 232 (e.g., a tube, such as a quartz tube) defining an internal flow volume 234 and a catalyst 236 (e.g., Fe@$SiO_2$) disposed within the volume 234.

Figure 2C:
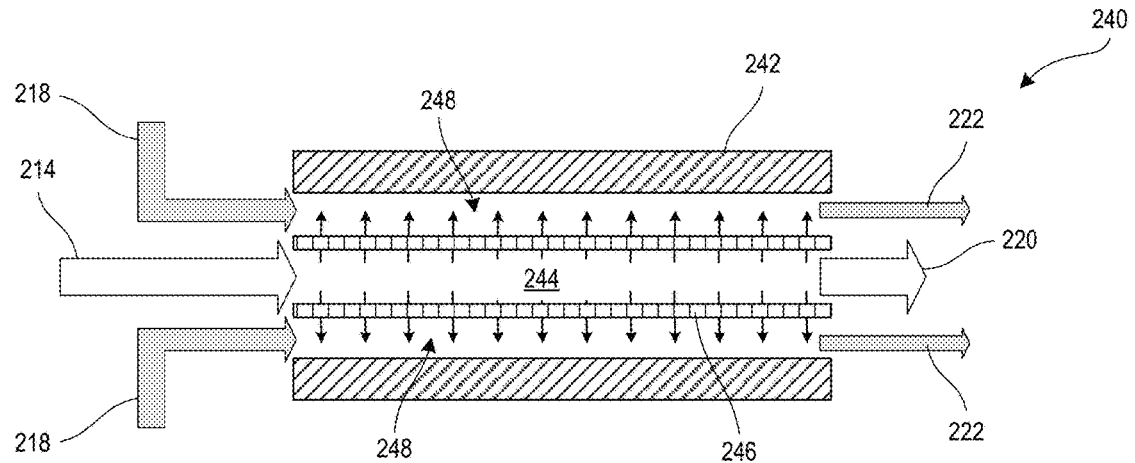
FIG. 2C is a simplified cross-sectional view of an exemplary tubular reactor setup that can be used for the hydrogen separator of FIG. 2A, according to one or more embodiments of the disclosed subject matter.
Figure 2D:
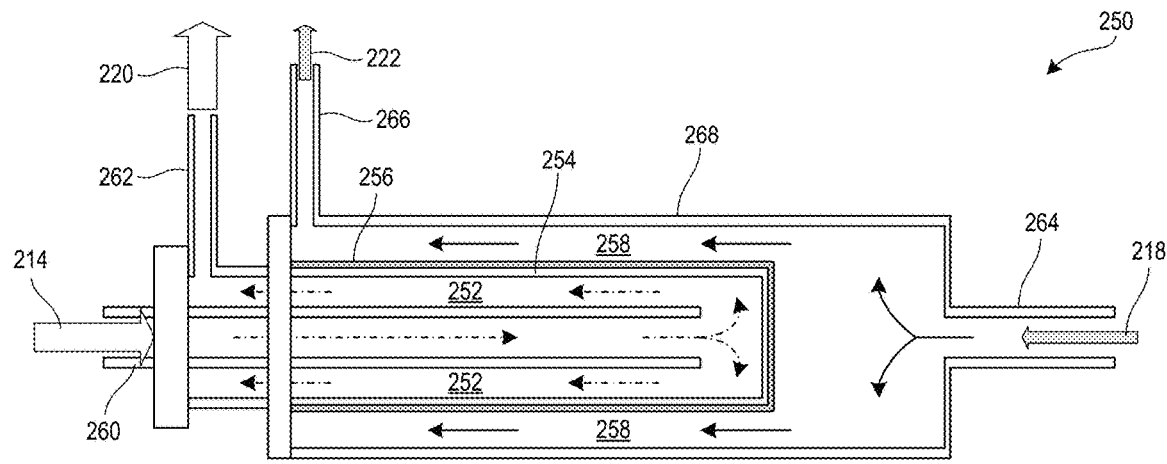
FIG. 2D is a simplified cross-sectional view of another exemplary tubular reactor setup that can be used for the hydrogen separator of FIG. 2A, according to one or more embodiments of the disclosed subject matter.
Figure 2E:
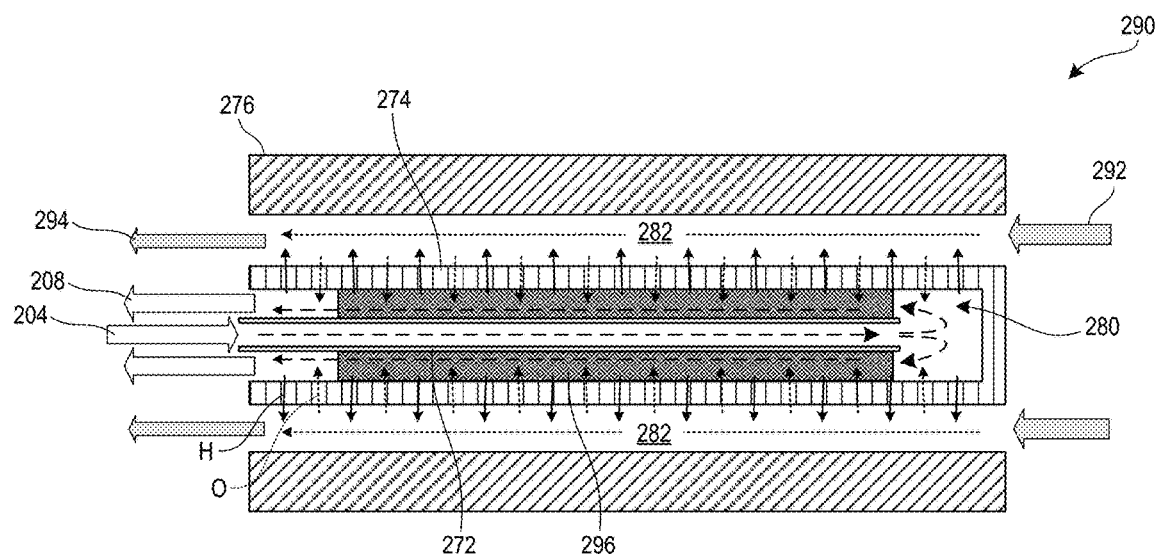
FIG. 2E is a simplified cross-sectional view of an exemplary tubular reactor setup for autothermal operation that can be used for the DNMC reactor of FIG. 2A, according to one or more embodiments of the disclosed subject matter.

In another example, FIG. 2E illustrates a tubular reactor setup 290 that can be used for the DNMC reactor 206 of FIG. 2A. The tubular reactor 290 can have a first gas volume 280 formed by the interior volume of a porous support tube 274. An $H_2$ permeable membrane (not separately illustrated) can be provided on a surface of the support tube 274, for example, on the radially outer surfaces of the support tube 274. The membrane can be constructed to allow protonic/electronic transport between the first and second gas volumes, such that $H_2$ produced from prior methane conversion can be removed from the first gas volume 280 to the second gas volume 282. Note that the $H_2$ transport through the membrane is via bulk diffusion, i.e., ion transport without application of an external electric field. For example, support tube can be a perovskite-type oxide having a formula of M'$Ce_{1-z}Zr_zO_{3-\delta}$, where M' is Sr or Ba, and z is between 0.01 and 0.3, inclusive, and the membrane can be a perovskite-type oxide having a formula of M'$Ce_{1-x-y}Zr_xM''_yO_{3-\delta}$, where M' is a least one of Sr and Ba; M''' is at least one of Ti, V, Cr, Mn, Fe, Co Ni, Cu, Nb, Mo, W, Pr, Nd, Pm, Sm, Eu, Gd, Tb, Dy, Ho, Er, Tm and Yb; x is between 0.01 and 0.2, inclusive; and y is between 0.01 and 0.3, inclusive. In some embodiments, the porous support tube is $SrCe_{0.8}Zr_{0.2}O_{3-\delta}$, and the $H_2$-permeable is a $SrCe_{0.7}Zr_{0.2}Eu_{0.1}O_{3\delta}$ film on the support tube. Other suitable materials for the permeable membrane and/or porous support can be found in, for example, U.S. Pat. No. 10,525,407, incorporated by reference above.

Feed gas can be provided to the first gas volume 280 via an inlet tube 272 disposed within the porous support tube 274. Inlet tube 272 can convey the input gas flow stream 204 to the first gas volume 280 and into contact with catalyst 296 (e.g., $Fe@SiO_2$). As illustrated in FIG. 2E, the porous support tube 274 can be provided with an end cap portion, which may be integral with the support tube 274 or a separate piece adhered to the support tube 274. The porous support tube 274 is thus closed at one end and opened at the other. The feed gas is thus redirected by the end cap back toward the inlet along the first gas volume 280 and through the catalyst 296 to thereby form first processed stream 208. Alternatively, the porous support tube 274 can be open at both ends, in which case the outlet can be disposed at end of the reactor 290 opposite from the inlet (e.g. similar to FIG. 2C).

The reactor 290 can have a second gas volume 282 formed by the annular space between the porous support tube 274 and an outer enclosure 276, e.g., a quartz tube. Sweep gas 292 can be provided to the second gas volume 282 and exits therefrom as outlet stream 294. In some embodiments, the sweep gas 292 can comprise an inert gas (e.g., $N_2$ or He). Alternatively, in some embodiments, the sweep gas 292 can comprise Oz gas or an oxygen containing compound. For example, the $CH_4$ can be converted to $C_{2+}$ products via the DNMC reaction in the reactor 290 following the equation $CH_4 \rightarrow 3/52\ C_6H_6 + 5/104\ C_{10}H_8 + 7/104\ C_2H_4 + 2/104\ C_2H_2 + 19/13\ H_2$ ($\Delta H > 0$). Meanwhile, outside of the tube 274, the $O_2$ in the sweep gas can react with $H_2$ permeate (e.g., $H_2 + \frac{1}{2}O_2 \rightarrow H_2O$, $\Delta H < 0$) to produce heat for the endothermic DNMC within the reactor tube. The energy balance between endothermic DNMC and exothermic $H_2$ combustion reactions on opposite sides of the membrane (e.g., supported on tube 274) can be achieved, thereby providing autothermal operation of DNMC. In some embodiments, back diffusion of $O_2$ from the sweep side (e.g., volume 282) to the DNMC side (e.g., volume 280) can oxidize carbon species into CO, thereby alleviating carbon deposition in the reactor 290 and avoiding coke formation.

Returning to FIG. 2A, the first processed stream 208 is directed to condenser 210, where the liquid aromatics in the stream 208 are removed from the effluent gases, for example, to the first output stream 212. The remaining effluent gases (e.g., $CH_4$, $H_2$, and $C_2$ products) are then directed as second processed stream 214 to an $H_2$ separator 216, which can have an $H_2$ permeable membrane. $H_2$ in the second processed stream 214 can be transported across the membrane (e.g., via permeation of hydrogen ions) in the $H_2$ separator 216 to produce pure $H_2$ via the membrane separation. For example, FIG. 2C illustrates a reactor setup 240 that can be used for $H_2$ separator 216 of FIG. 2A. Reactor 240 can be configured as a tubular reactor, with an inner tube 246 defining a first gas volume 244 for the second processed stream 214 and an annular space 248 between the inner tube 246 and an outer tube 242 serving as a second gas volume for sweep gas 218. A wall of the inner tube 246 can be formed with the permeable membrane thereon, such that the reactor can be considered a flow-through tubular membrane reactor. Alternatively, an end-capped reactor setup 250 can be used for $H_2$ separator 216 of FIG. 2A, for example, as shown in FIG. 2D. Reactor 250 can also be configured as a tubular reactor with a first gas volume 252 formed by the interior volume of a porous support tube 254. An $H_2$ permeable membrane 256 can be provided on a surface of the support tube 254, for example, on the radially outer surfaces of the support tube 254. In the examples of FIGS. 2C-2D, the support tube, the membrane, or both can be formed similar to that described above for the reactor setup 290 of FIG. 2E.

Returning to FIG. 2D, second processed stream 214 can be provided to the first gas volume 252 via an inlet tube 260 disposed within the porous support tube 254. Inlet tube 260 can convey the second processed stream 214 to the first gas volume 252. The porous support tube 254 can be provided with an end cap portion, such that the tube 254 is closed at one end and opened at the other. The second processed stream is thus redirected by the end cap back toward the inlet along the first gas volume 252, whereby $H_2$ can permeate through the membrane 256 to the second gas volume 258, to thereby form effluent stream 220 exiting via first outlet 262. The second gas volume 258 can be formed by the annular space between the porous support tube 254 and an outer enclosure 268, e.g., a quartz tube. Sweep gas 218 can be provided to the second gas volume 258 via inlet 264 and exits as output stream 222 via second outlet 266.

In some embodiments of the reactor 240 of FIG. 2C or the reactor 250 of FIG. 2D, the sweep gas provided to the second gas volume can comprise an inert gas (e.g., such as nitrogen, helium, neon, argon, krypton, xenon, radon, or combinations thereof). Alternatively, in some embodiments, the sweep gas can comprise $O_2$ gas (e.g., air, $O_2$ gas alone, or $O_2$ gas combined with one or more other gases) or an oxygen containing compound (e.g., $CO_2$, $H_2O$, and/or alcohol). The oxygen in the sweep gas can react with hydrogen that has permeated through the membrane to the second gas volume to produce heat within the reactor tube, for example, in a manner similar to that described above for reactor 290 of FIG. 2E.

Returning to FIG. 2A, the effluent 220 from the $H_2$ separator 216 can then be recycled back to input gas flow stream 204, via recycle line 224, for introduction into the DNMC reactor 206 in a subsequent cycle. By increasing the number of cycles, $CH_4$ conversion can be increased significantly beyond the first pass equilibrium, and high aromatic liquid yields can be achieved. Moreover, the decoupling of $CH_4$ activation and $H_2$ separation into two operation units can improve carbon conversion efficiency, since heavier aromatic hydrocarbon products could have grown under DNMC reaction conditions to coke, which would otherwise deteriorate membrane performance and reduce $CH_4$-to-aromatics conversion efficiency.

Although FIGS. 2B-2E illustrate specific configurations for components of system 200, other reactor configurations and variations (e.g., to provide multiple reactors operating in series, in parallel, or both, for example, to scale up to process practical quantities of methane) are also possible according to one or more embodiments of the disclosed subject matter. For example, any of the membrane reactor configurations disclosed in U.S. Pat. No. 10,525,407, incorporated by reference above, can be used in place of the DNMC reactor 206, the $H_2$ separator 216, and/or any other reactor disclosed herein.

Methane Conversion Method

Figure 3:
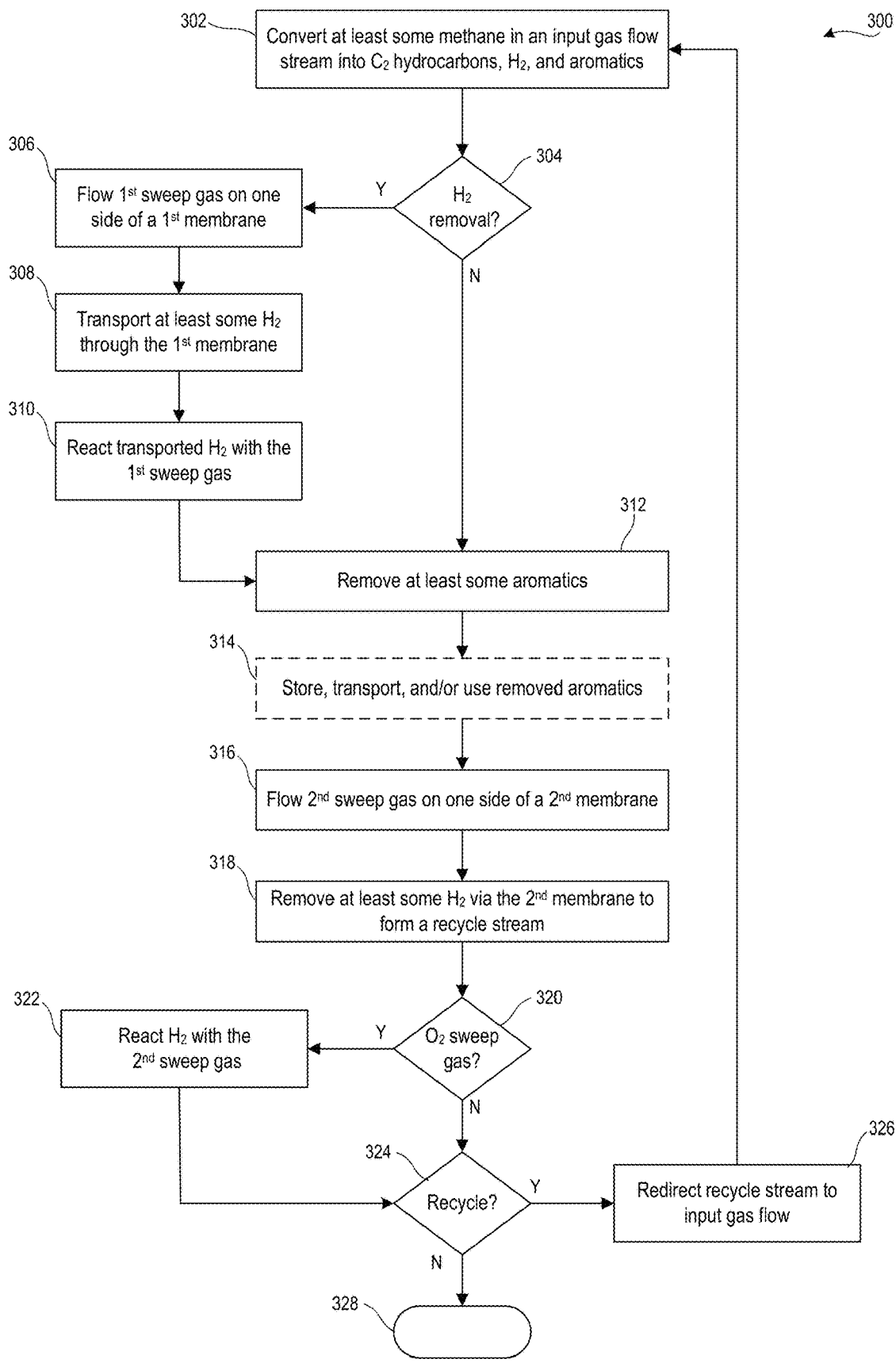
FIG. 3 is a process flow diagram for a method of methane conversion with gas recycle, according to one or more embodiments of the disclosed subject matter.

FIG. 3 is a process flow diagram for an exemplary method 300 of methane conversion with gas recycle. The method 300 can initiate at process block 302, where at least some methane in an input gas flow stream is converted into $C_2$ hydrocarbons, $H_2$, and aromatics via interaction with a catalyst at an elevated temperature. For example, the methane conversion can comprise DNMC. In some embodiments, the methane conversion can be performed by or within one or more first reactors, such as any of reactors 106, 184, 186, 206, 230, 290, and 410. The methane conversion can occur at a first temperature, for example, at least 1000 K (e.g., ≥1200 K). In some embodiments, the conversion of process block 302 can produce a first processed stream comprising the $C_2$ hydrocarbons, $H_2$, aromatics, and any unreacted methane.

The method 300 can proceed to decision block 304, where it is determined if hydrogen should be removed prior to aromatics separation. If it is desired to remove hydrogen, the method 300 can proceed from decision block 304 to process block 306, where a first sweep gas can be flowed on a first side (e.g., within a second gas flow volume) of a first membrane (e.g., of the first reactor) opposite to the input gas flow stream and/or the first processed stream (e.g., within a first gas flow volume). In some embodiments, the first sweep gas can comprise $O_2$ or an oxygen-containing compound. The method 300 can proceed to process block 308, where at least some of the $H_2$ produced by the methane conversion is transported (e.g., via permeation of hydrogen ions) across the first membrane (e.g., from the first gas flow volume to the second gas flow volume). The method 300 can then proceed to process block 310, where the transported $H_2$ (e.g., in the second gas flow volume) reacts with the first sweep gas, for example, to combust the permeated hydrogen with oxygen in the sweep gas to form water and to generate heat that can drive, at least in part, the methane conversion of process block 302.

After process block 310, or if it was not desired to remove hydrogen at decision block 304, the method 300 can proceed to process block 312, where at least some aromatics can be removed from the first processed stream. For example, aromatics can be removed from (e.g., separated from) the first processed stream via condensing the aromatics into a liquid while other components of the first processed stream remain in gas form. In some embodiments, the aromatics removal can be performed by or within one or more aromatics separation devices, such as any of device 114, device 164, condenser 210, heat exchanger 414, chiller 418, and condenser 422. In some embodiments, the removal of process block 312 can produce a second processed stream comprising the $C_2$ hydrocarbons, any unreacted methane, and any aromatics and/or $H_2$ not previously removed.

The method 300 can proceed to optional process block 314, where the removed aromatics (e.g., in liquid form) can be stored, transported, and/or used. For example, the liquid aromatics can be stored in a container that is releasably coupled or fixedly coupled to an aromatics separation device. The method 300 can proceed to process block 316, where a second sweep gas can be flowed on a first side (e.g., within a second gas flow volume) of a second membrane (e.g., of a second reactor) opposite to the second processed stream and/or a resulting product stream (e.g., within a first gas flow volume. In some embodiments, the second sweep gas can comprise an inert gas. Alternatively or additionally, in some embodiments, the second sweep gas can comprise $O_2$ or an oxygen-containing compound.

The method 300 can proceed to process block 318, where at least some of the $H_2$ in the second processed stream is removed. For example, the $H_2$ removal can comprise permeation of hydrogen ions through the second membrane (e.g., from the first gas flow volume to the second gas flow volume). In some embodiments, the $H_2$ removal can be performed by or within one or more second reactors, such as any of reactor 126, reactor 194, reactor 196, separator 216, reactor 240, reactor 250, and separator 430. The $H_2$ removal can occur at a second temperature, for example, less than 1000 K (e.g., ≤800 K). In some embodiments, the removal of process block 318 can produce a product stream comprising the $C_2$ hydrocarbons, any unreacted methane, and potentially any $H_2$ and aromatics not previously removed.

Proceeding to decision block 320, if the second sweep gas comprises $O_2$ or an oxygen-containing compound, the method 300 can proceed to process block 322, where the removed $H_2$ (e.g., in the second gas flow volume) reacts with the second sweep gas, for example, to combust the permeated hydrogen with oxygen in the second sweep gas to form water and to generate heat that can drive, at least in part, the hydrogen permeation of process block 318 and/or the further conversion of methane by the second reactor. After process block 322, or if the sweep gas did not comprise $O_2$ or an oxygen-containing compound at decision block 320, the method 300 can proceed to decision block 324.

At decision block 324, it is determined whether the product stream resulting from process block 318 should be re-processed, for example, to increase methane conversion and/or aromatic yield by subjecting the product stream to another cycle of conversion, aromatic separation, and $H_2$ removal. If re-processing is desired, the method 300 can proceed from decision block 324 to process block 326, where the product stream is redirected to be used as the input gas flow stream to the first reactor (or combined with additional methane for use as the input gas flow stream). The method 300 can then return to process block 302. Otherwise, if re-processing is not desired (e.g., if all of the methane has been converted or further methane conversion is not possible), the method 300 can proceed from decision block 324 to terminal 328, where the method can end.

Although illustrated separately, it is contemplated that various process blocks may occur simultaneously or iteratively. For example, the methane conversion 302, $H_2$ transport 308 or 318, sweep gas flow 306 or 316, aromatics removal 312, and $H_2$ reaction 310 or 322 can occur simultaneously despite being illustrated as sequential process blocks. Furthermore, certain process blocks illustrated as occurring after others may indeed occur before. For example, a sweep gas flow 306 or 316 may be initiated before any initiation of methane conversion 302. Although some of blocks 302-328 of method 300 have been described as being performed once, in some embodiments, multiple repetitions of a particular process block may be employed before proceeding to the next decision block or process block. In addition, although blocks 302-328 of method 300 have been separately illustrated and described, in some embodiments, process blocks may be combined and performed together (simultaneously or sequentially). Moreover, although FIG. 3 illustrates a particular order for blocks 302-328, embodiments of the disclosed subject matter are not limited thereto. Indeed, in certain embodiments, the blocks may occur in a different order than illustrated or simultaneously with other blocks.

Methane Conversion System

Figure 4:
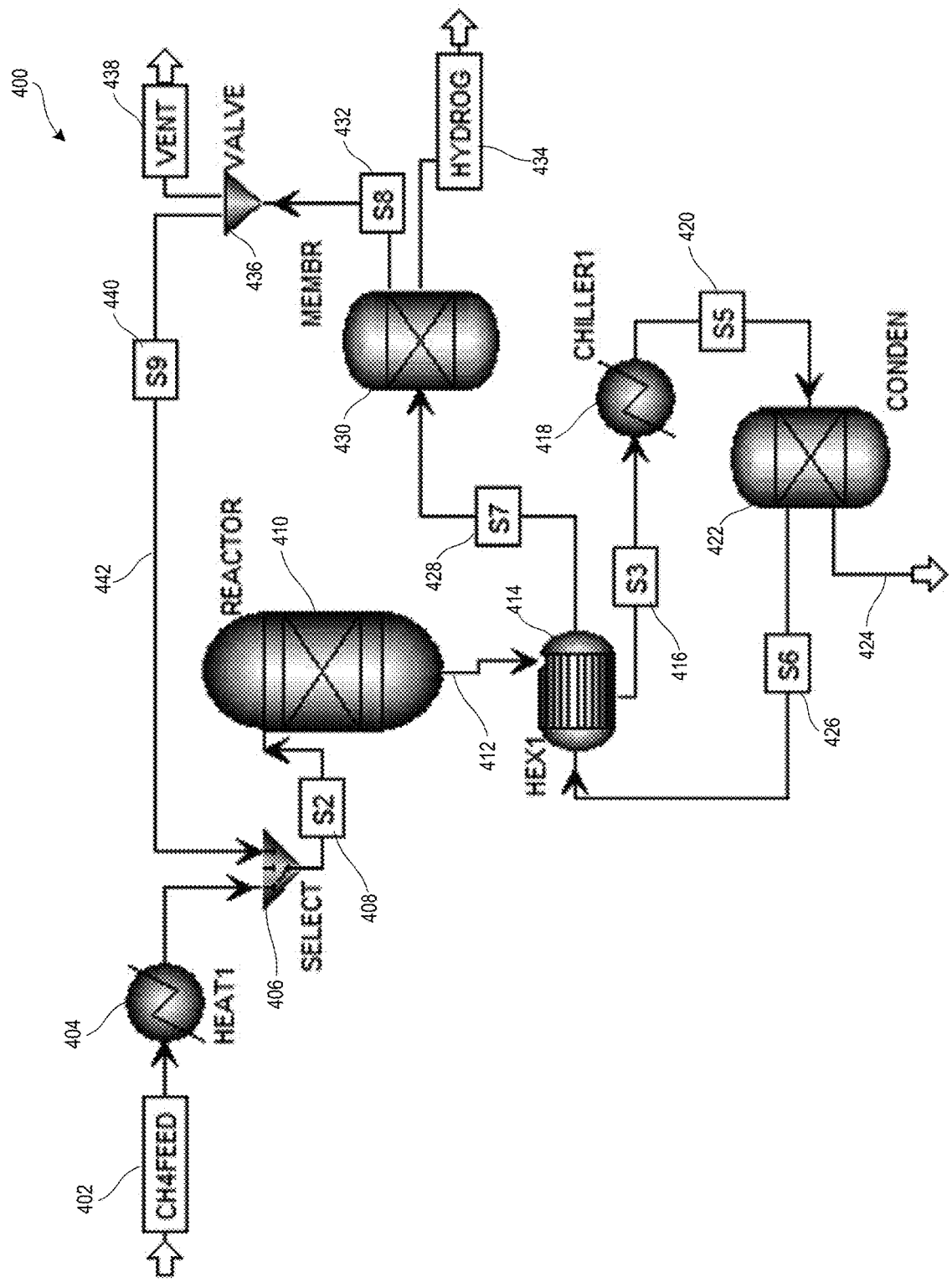
FIG. 4 is a simplified schematic diagram illustrating another exemplary configuration for a gas-recycle system with DNMC reactor and hydrogen separator, according to one or more embodiments of the disclosed subject matter.

FIG. 4 illustrates a more detailed configuration of an exemplary gas recycle system 400. In the illustrated example, gas recycle system 400 includes a first heat exchanger 404, a feed coupler 406, a DNMC reactor 410, a second heat exchanger 414, a chiller 418, a condenser 422, an $H_2$ membrane separator 430, and a valve 436. In operation of system 400, a methane feed stream 402 can be provided to first heat exchanger 404, which can serve to preheat the methane prior to introduction into the DNMC reactor 410. The methane stream can be directed from the first heat exchanger 404 via feed coupler 406 as input flow stream 408 to the DNMC reactor 410. The feed coupler 406 can select between the fresh methane feed stream or the recycle stream 440 (e.g., product stream 432 via valve 436 and recycle line 442) for introduction to the DNMC reactor 410. Within the DNMC reactor 410, at least some of the methane in input flow stream 408 can be converted to $C_2$ hydrocarbons, $H_2$, and aromatics. A first processed stream 412 comprising any unreacted methane along with the produced $C_2$ hydrocarbons, $H_2$, and aromatics can be output from the DNMC reactor 410.

The first processed stream 412 can be passed through second heat exchanger 414 (e.g., cross-flow heat exchanger) to cool the first stream 412. In the illustrated example, the cooling of the first processed stream 412 serves to preheat the second processed stream 426 prior to introduction to the $H_2$ separator 430, thereby providing heat recovery. The resulting cooled stream 416 is directed to chiller 418, which serves to further reduce the temperature of the stream in preparation for aromatics separation. The further cooled stream 420 is then directed to condenser 422, which condenses at least some of the aromatics out of the stream, thereby forming a first output stream 424 of liquid aromatics and a second processed stream 426 of unreacted methane, $H_2$, and $C_2$ hydrocarbons (and any aromatics not removed by condenser 422). In some embodiments, the heat exchanger 414, chiller 418, and/or condenser 422 may be considered components of an aromatics separation device or module.

As noted above, the second processed stream 426 is passed through the second heat exchanger 414 for preheating by heat recovery from the first processed stream 412. The resulting preheated stream 428 is directed to $H_2$ separator 430, where at least some $H_2$ in the preheated stream 428 can be removed from the stream, for example, via permeation of hydrogen through a membrane, thereby forming a second output stream 434 of pure hydrogen (e.g., permeated $H_2$ product) and a product stream 432 of unreacted methane and $C_2$ hydrocarbons (and any aromatics and/or $H_2$ not previously removed). The product stream 432 can be directed for re-processing by the system 400 (e.g., in another cycle) via valve 436 and recycle line 442. Alternatively, if re-processing is not desired (e.g., if all methane has been converted and/or further methane conversion is not possible), then the valve 436 can redirect the product stream 432 to vent 438, for example, for release to atmosphere or directed for storage, use, or disposal.

System 400 can include additional components beyond those specifically illustrated in FIG. 4 or described above. For example, system 400 can include a controller, a heater or furnace, temperature sensors, flow sensors, flow controllers, pumps, etc.

Computer Implementation

Figure 5:
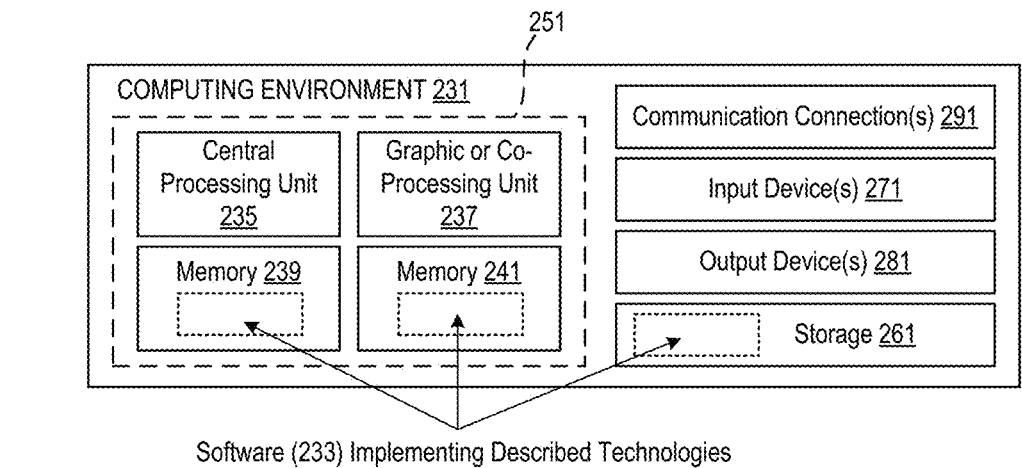
FIG. 5 depicts a generalized example of a computing environment in which the disclosed technologies may be implemented.

FIG. 5 depicts a generalized example of a suitable computing environment 231 in which the described innovations may be implemented, such as controller 140, a controller of system 200, a controller of system 400, or method 300. The computing environment 231 is not intended to suggest any limitation as to scope of use or functionality, as the innovations may be implemented in diverse general-purpose or special-purpose computing systems. For example, the computing environment 231 can be any of a variety of computing devices (e.g., desktop computer, laptop computer, server computer, tablet computer, etc.).

With reference to FIG. 5, the computing environment 231 includes one or more processing units 235, 237 and memory 239, 241. In FIG. 5, this basic configuration 251 is included within a dashed line. The processing units 235, 237 execute computer-executable instructions. A processing unit can be a central processing unit (CPU), processor in an application-specific integrated circuit (ASIC) or any other type of processor (e.g., hardware processors, graphics processing units (GPUs), virtual processors, etc.). In a multi-processing system, multiple processing units execute computer-executable instructions to increase processing power. For example, FIG. 5 shows a central processing unit 235 as well as a graphics processing unit or co-processing unit 237. The tangible memory 239, 241 may be volatile memory (e.g., registers, cache, RAM), non-volatile memory (e.g., ROM, EEPROM, flash memory, etc.), or some combination of the two, accessible by the processing unit(s). The memory 239, 241 stores software 233 implementing one or more innovations described herein, in the form of computer-executable instructions suitable for execution by the processing unit(s).

A computing system may have additional features. For example, the computing environment 231 includes storage 261, one or more input devices 271, one or more output devices 281, and one or more communication connections 291. An interconnection mechanism (not shown) such as a bus, controller, or network interconnects the components of the computing environment 231. Typically, operating system software (not shown) provides an operating environment for other software executing in the computing environment 231, and coordinates activities of the components of the computing environment 231.

The tangible storage 261 may be removable or non-removable, and includes magnetic disks, magnetic tapes or cassettes, CD-ROMs, DVDs, or any other medium which can be used to store information in a non-transitory way, and which can be accessed within the computing environment 231. The storage 261 can store instructions for the software 233 implementing one or more innovations described herein.

The input device(s) 271 may be a touch input device such as a keyboard, mouse, pen, or trackball, a voice input device, a scanning device, or another device that provides input to the computing environment 231. The output device(s) 271 may be a display, printer, speaker, CD-writer, or another device that provides output from computing environment 231.

The communication connection(s) 291 enable communication over a communication medium to another computing entity. The communication medium conveys information such as computer-executable instructions, audio or video input or output, or other data in a modulated data signal. A modulated data signal is a signal that has one or more of its characteristics set or changed in such a manner as to encode information in the signal. By way of example, and not limitation, communication media can use an electrical, optical, radio-frequency (RF), or another carrier.

Any of the disclosed methods can be implemented as computer-executable instructions stored on one or more computer-readable storage media (e.g., one or more optical media discs, volatile memory components (such as DRAM or SRAM), or non-volatile memory components (such as flash memory or hard drives)) and executed on a computer (e.g., any commercially available computer, including smart phones or other mobile devices that include computing hardware). The term computer-readable storage media does not include communication connections, such as signals and carrier waves. Any of the computer-executable instructions for implementing the disclosed techniques as well as any data created and used during implementation of the disclosed embodiments can be stored on one or more computer-readable storage media. The computer-executable instructions can be part of, for example, a dedicated software application or a software application that is accessed or downloaded via a web browser or other software application (such as a remote computing application). Such software can be executed, for example, on a single local computer (e.g., any suitable commercially available computer) or in a network environment (e.g., via the Internet, a wide-area network, a local-area network, a client-server network (such as a cloud computing network), or any other such network) using one or more network computers.

For clarity, only certain selected aspects of the software-based implementations are described. Other details that are well known in the art are omitted. For example, it should be understood that the disclosed technology is not limited to any specific computer language or program. For instance, aspects of the disclosed technology can be implemented by software written in C++, Java™, Python®, or any other suitable computer language. Likewise, the disclosed technology is not limited to any particular computer or type of hardware. Certain details of suitable computers and hardware are well known and need not be set forth in detail in this disclosure.

It should also be well understood that any functionality described herein can be performed, at least in part, by one or more hardware logic components, instead of software. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

Furthermore, any of the software-based embodiments (comprising, for example, computer-executable instructions for causing a computer to perform any of the disclosed methods) can be uploaded, downloaded, or remotely accessed through a suitable communication means. Such suitable communication means include, for example, the Internet, the World Wide Web, an intranet, software applications, cable (including fiber optic cable), magnetic communications, electromagnetic communications (including RF, microwave, and infrared communications), electronic communications, or other such communication means. In any of the above-described examples and embodiments, provision of a request (e.g., data request), indication (e.g., data signal), instruction (e.g., control signal), or any other communication between systems, components, devices, etc. can be by generation and transmission of an appropriate electrical signal by wired or wireless connections.

Fabricated Examples and Experimental Results

Gas Recycle System

To test performance of the gas-recycle system (e.g., having a setup similar to that shown in FIG. 2A) with respect to $CH_4$ conversion and aromatics liquid yield, the DNMC reactor (e.g., reactor 206 in FIG. 2A) and the $H_2$-permeable membrane separator (e.g., separator 216 in FIG. 2A) were investigated separately with simulated feeds in each cycle. The DNMC reactor was formed as a fixed-bed quartz tube (e.g., in a configuration similar to reactor 230 shown in FIG. 2B, with a 7-mm inner diameter), in which 0.3750 g Fe@$SiO_2$ catalyst was packed for methane activation. The DNMC reaction was run at atmospheric pressure and 1303 K in the DNMC reactor, which was controlled using a furnace (Applied Test Systems Series 3210) connected to a controller (Eurotherm Temperature Controller, 3216 series). Catalyst temperatures were measured using a K-type thermocouple touching the middle of the catalyst bed on the external surface of the quartz tube. In the first cycle of the experiment, the catalyst was heated to the reaction temperature at a ramp rate of 10 K/min in argon (Ar) flow (20 mL/min). Afterward, the gas flow was switched to a reaction gas mixture (20 mL/min, 90% $CH_4$ and 10% Ar). The product effluents were analyzed on-line by a gas chromatograph (Agilent 6890) containing a (5%-Phenyl)-methylpolysiloxane capillary column (HP-5, 30.0 m×0.25 mm×0.25 µm) connected to a flame-ionization detector (FID) and a packed column (ShinCarbon ST Columns, 80/100 mesh, 1.83-m) linked to a thermal conductivity detector (TCD). Transfer lines were maintained at temperatures greater than 473 K by resistive heating to prevent any condensation. In the second and follow-on reaction cycles, the feed gas was a mixture of $H_2$, $CH_4$ and Ca hydrocarbons, whose composition and flow rate were determined from the preceding gas flow stream after passing through an aromatics condenser and $H_2$-separator. The products were analyzed using the same set-up and method as those for the first cycle of the experiment.

The $H_2$ separator was an $H_2$-permeable perovskite ceramic membrane tube (e.g., in a configuration similar to reactor 240 shown in FIG. 2C) that comprised a porous $SrCe_{0.8}Zr_{0.2}O_{3-\delta}$ support and a thin and dense $H_2$-permeable $SrCe_{0.7}Zr_{0.2}Eu_{0.1}O_{3\delta}$ film on the porous support. The $SrCe_{0.8}Zr_{0.2}O_{3-\delta}$ perovskite ceramic is a mixed ionic and electronic conductor (MIEC), which means internal electronic transport balances the protonic transport eliminating the need for an external electric circuit to enable $H_2$ separation. The $H_2$-permeable membrane tube was prepared by tape casting a $SrCe_{0.8}Zr_{0.2}O_3$ slurry and rolling end-capped tubular-type supports, followed by colloidal coating a thin dense $SrCe_{0.7}Zr_{0.2}Eu_{0.1}O_{3\delta}$ layer on the porous support. For the $H_2$ permeation test of the $H_2$ separator, the feed side (inside of the membrane tube) was exposed to $H_2$ diluted to the tested concentration using an Ar tracer. The total flow rate of the feed gas (mixture of $H_2$ and Ar) was set at 20 mL/min. The sweep side (outside of the membrane tube) was exposed to 5% $N_2$/He at 20 mL/min and connected to the gas chromatograph (Agilent 6890) to quantify the permeated $H_2$. In addition to being a diluent, the Ar in the feed gas was used as a tracer to confirm no trans-membrane leak, which would be indicated by an increase in Ar signal of the gas chromatograph.

The composition of simulated feed for the DNMC reactor was determined from the stream in the previous cycle after passing through the aromatics liquid condenser and $H_2$ membrane separator. The composition of feed for the $H_2$ separator was set the same as the product effluent from the DNMC reactor in the same cycle, except that all the aromatics were condensed and separated from the effluent. Finally, the DNMC reactor and $H_2$ membrane separator together with an aromatics liquid condenser were simulated by Aspen Plus® to analyze the system feasibility for $CH_4$ upgrading via the DNMC process.

Figure 6A:
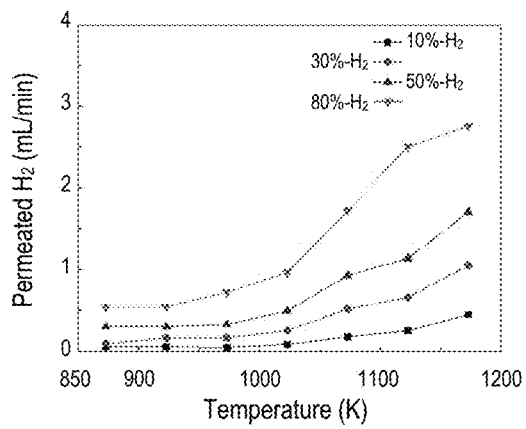
FIGS. 6A-6B are graphs of $H_2$ permeation flux and $H_2$ removal efficiency, respectively, through a single $SrCe_{0.7}Zr_{0.2}Eu_{0.1}O_{3-\delta}$ membrane tube as a function of test temperature and $H_2$ partial pressure.
Figure 6B:
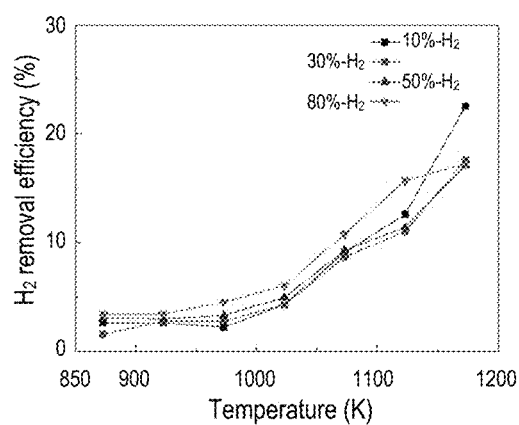

To understand the membrane $H_2$ removal capability from the gas recycle, the $H_2$ permeation fluxes at different temperatures and $H_2$ partial pressures were determined for a feed flow rate of 20 ml/min ($H_2$ concentration varied, balanced by Ar) and a sweep side flow rate of 20 ml/min (5% $N_2$ balanced by He). FIG. 6A shows that the permeated $H_2$ fluxes as a function of separator temperature and $H_2$ partial pressure in the feed side in a single membrane tube. With increasing temperature or $H_2$ partial pressure, the $H_2$ flux increased. This is caused by the increasing ambipolar ionic/electronic conductivity of the MIEC $SrCe_{0.7}Zr_{0.2}Eu_{0.1}O_{3\delta}$ membrane at high temperature or high partial pressure of $H_2$ feed. From the flow rate of $H_2$ feed and $H_2$-permeation flux, the $H_2$ removal efficiency, indicated by the ratio of $H_2$-permeation flux/$H_2$ feed, at each condition was evaluated, as shown in FIG. 6B.

The $H_2$ removal efficiency does not depend on the $H_2$ concentration in the feed, but it does depend on the temperature. When the temperature was increased from 873 K to 1173 K, the $H_2$ removal efficiency was increased from 2.67% to 18.60%, equivalent to ~7 times higher enhancement in $H_2$ removal efficiency at the same $H_2$ feed condition. Therefore, in some cases, high temperature can be used to remove $H_2$ more efficiently from the $H_2$-permeable $SrCe_{0.7}Zr_{0.2}Eu_{0.1}O_{3\delta}$ membrane separator. The $SrCe_{0.7}Zr_{0.2}Eu_{0.1}O_{3\delta}$ membrane tube had an inner diameter of 7 mm and a length of 15 cm; however, only 20% (~3 cm) of the membrane tube length was kept at the test temperature due to the thermal gradient of the tubular furnace that supplied heat to the membrane. Thus, the $H_2$-permeation flux could be significantly higher compared to the present $H_2$ flux data of FIGS. 6A-6B if the entire membrane tube was kept at the test temperature. The $H_2$ flux can be enhanced significantly if operated under a pressure gradient and the total $H_2$ permeance area increased by use of a membrane tube bundle.

Figure 7A:
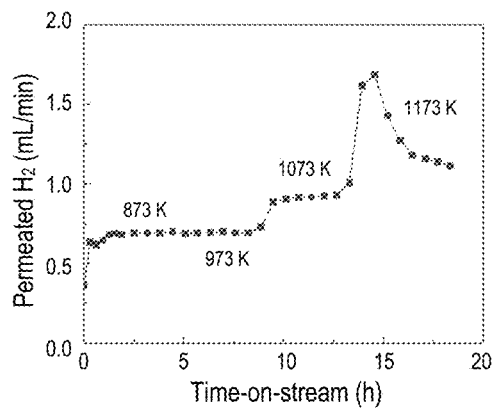
FIGS. 7A-7B are graphs of $H_2$ permeation flux and $H_2$ removal efficiency, respectively, of the $SrCe_{0.7}Zr_{0.2}Eu_{0.1}O_{3-\delta}$ membrane tube at different temperatures as a function of time on stream.
Figure 7B:
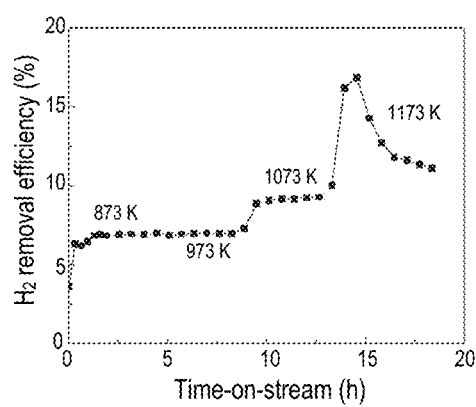

In the gas recycle system, the $H_2$ removal stage takes place after the DNMC reaction in the DNMC reactor. The feed to the $H_2$ separator thus contains both $H_2$ and hydrocarbons (e.g., unreacted $CH_4$ and $C_2$ products), which feed is slightly different from the feed conditions examined to produce FIGS. 6A-6B. In order to test the effect of hydrocarbons in the $H_2$ feed stream on the performance of the $H_2$ membrane, a control experiment was performed by adding 5% $CH_4$ into the $H_2$ feed in the permeation tests, with a feed flow rate feed flow rate of 20 ml/min (50% $H_2$+5% $CH_4$, balanced by Ar) and a sweep side flow rate of 20 ml/min (5% $N_2$ balanced by He). As shown in FIG. 7A-7B, the $H_2$ permeation flux increased with increasing temperature, even in the presence of $CH_4$ in the feed. When the temperature was set at 1173 K, a reduction of the $H_2$ flux was observed, which may be caused by carbon deposition on the membrane surface. For example, at high temperatures (e.g., >1100 K), the $SrCe_{0.7}Zr_{0.2}Eu_{0.1}O_{3-\delta}$ membrane materials could cause $CH_4$ activation to coking species, and thus lead to lower $H_2$ flux. This confirms the advantages of decoupling the $CH_4$ reaction and $H_2$ separation by separating into two different stages (e.g., operation units), since DNMC requires high temperature (e.g., >1100 K) to reach appreciable $CH_4$ conversion and $C_{2+}$ yield that would otherwise cause the $SrCe_{0.7}Zr_{0.2}Eu_{0.1}O_{3\delta}$ membrane performance to deteriorate with respect to $H_2$ permeation. However, these results apply to the test membrane, and may not be indicative of all membranes. Moreover, as described above and in further detail below, the use of a sweep gas comprising $O_2$ or an oxygen-containing compound can prevent, or at least reduce, coke formation on the membrane and thereby allow the $H_2$ separation membrane to operate at higher temperatures (e.g., higher than an operating temperature of the catalyst).

It should be noted that the $H_2$ flux in FIG. 7A was stable up to 1073 K. Moreover, the $H_2$ permeation flux at 1073 K in the experiments underlying FIG. 7A was the same as that of 50% $H_2$ feed (balanced by Ar and in the absence of $CH_4$ hydrocarbon) in the experiments underlying FIG. 6A. Therefore, for the remaining $H_2$ permeation tests for the gas recycle system, the temperature of the $H_2$ membrane separator was set at 1073 K, and the $H_2$ removal efficiency at this condition was 10% whether hydrocarbons were present or not in the feed to the $H_2$ membrane.

Figure 8A:
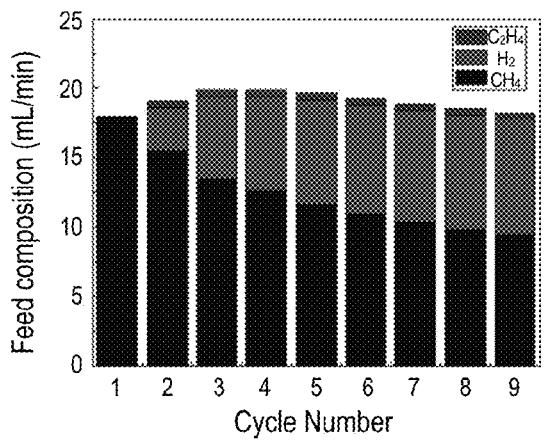
FIGS. 8A-8D are graphs of feed composition and flow rates to the methane reactor at different cycle numbers for $H_2$ removal efficiencies by the hydrogen separator of 10% $H_2$ removal, 40% $H_2$ removal, 70% $H_2$ removal, and 100% $H_2$ removal, respectively.
Figure 9A:
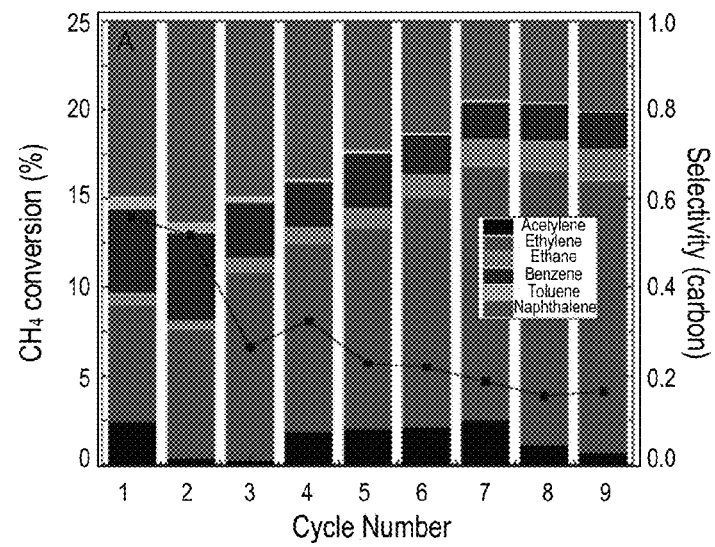
FIGS. 9A-9D are graphs of methane conversion and product selectivity after the methane reactor at different cycle numbers for $H_2$ removal efficiencies by the hydrogen separator of 10% $H_2$ removal, 40% $H_2$ removal, 70% $H_2$ removal, and 100% $H_2$ removal, respectively.

To examine the performance of the $CH_4$ reaction in the gas recycle system, the feed and exit effluent compositions of the DNMC reactor were measured, which compositions can change depending on the recycle number of the process. Therefore, the gas compositions and gas flow rates in each cycle were measured before the overall performance of the gas recycle system was analyzed. In DNMC, the gas feed was started (i.e., in the first cycle) with 90% $CH_4$ mixed with 10% Ar internal standard at a flow rate of 20 mL/min, as shown in FIG. 8A. At the reaction temperature of 1303 K, the DNMC reactor achieved 14.0% $CH_4$ conversion, 5.4% $C_2$ product yield, and 8.5% aromatics yield, as shown in FIG. 9A. The DNMC over Fe@$SiO_2$ catalyst showed stable $CH_4$ conversion and product selectivity. Assuming all aromatics products are removed via a condenser after the DNMC reactor, the feed to the $H_2$ separator would be comprised of unreacted $CH_4$, $C_2$ hydrocarbons, and $H_2$ gas in the effluents of the methane reactor. On the basis of the $H_2$ removal efficiency of the $H_2$ separator in FIGS. 6A-6B, the effluents after the $H_2$ separator are then fed to the DNMC reactor in the subsequent cycle.

Since ethylene ($C_2H_4$) is the predominant $C_2$ product, as shown in FIG. 9A, the Ca species in the effluent gases after the $H_2$ separator were assumed to be $C_2H_4$. Therefore, the gas feed for the subsequent cycles for the DNMC reactor in the gas recycle system was composed of $CH_4$, $C_2H_4$, and $H_2$. For example, after the DNMC reactor (14.0% $CH_4$ conversion) and $H_2$ separator (10.0% $H_2$ removal efficiency) in the first cycle in the experimental setup, the feed to DNMC reactor was comprised of a gas mixture of $CH_4/C_2H_4/H_2$ at a molar ratio of 1.00/0.03/0.20 and at a flow rate of 19.13 mL/min. Following the same analysis described above, FIG. 8A shows the composition and flow rate of the feed gas to the DNMC reactor at each cycle number at 10% $H_2$ removal efficiency by the $H_2$ separator in each cycle. It can be seen that the flow rate of gas mixture $CH_4/C_2H_4/H_2$ increased and then decreased with the cycle number. In the third cycle, the gas mixture flow rate was increased to the maxima (19.87 mL/min, equivalent to a 9.32% increase compared to the 18.00 mL/min flow rate in the first cycle). Up to the ninth cycle, the gas mixture flow rate was still 1.00% higher than the feed flow rate in the first cycle. The gas composition in the feed to the DNMC reactor changes with the cycle number. With increasing reaction cycle, the $CH_4$ composition was monotonically decreased, $H_2$ concentration had an opposite trend, and $C_2H_4$ concentration (~2.40%) was nearly constant independent of the reaction cycle. At the ninth reaction cycle, the $CH_4$ flow rate dropped to 51.80% of the $CH_4$ feed in the first cycle, which indicates the rest of $CH_4$ (~49.20%) has been converted to aromatics liquids after nine reaction cycles.

Figure 8B:
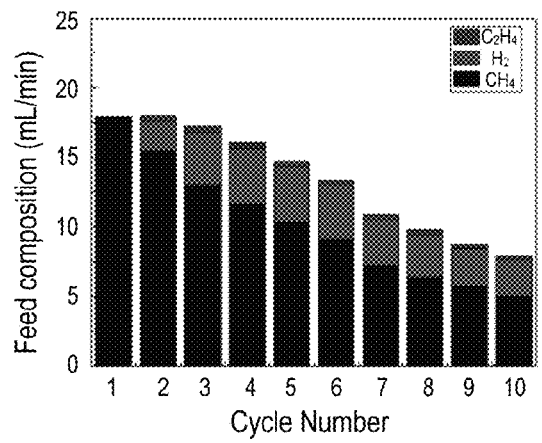
Figure 8C:
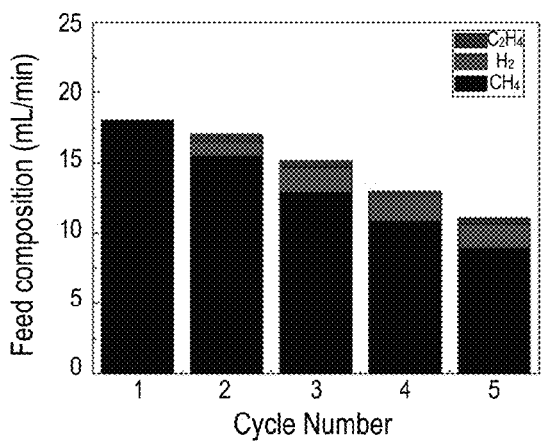
Figure 8D:
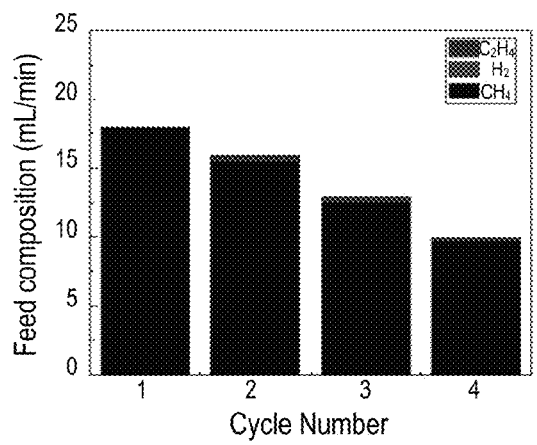

Although the single $H_2$ separator tube in the experiments exhibited only 10% $H_2$ removal efficiency, further enhancement in $H_2$ removal efficiency can be achieved, for example, as described elsewhere herein. To test how $H_2$ removal efficiency affects the performance of the DNMC reactor in the gas recycle system, the composition and flow rate of $CH_4/C_2H_4/H_2$ feed mixture in each cycle was analyzed by assuming the $H_2$ separator reaches 40%, 70%, and 100% $H_2$ removal efficiency, respectively. As shown in FIGS. 8B-8D, the total gas flow rate decreased with increasing $H_2$ removal efficiency in the $H_2$ separator unit at the same cycle. With increasing $H_2$ removal efficiency at the same cycle, the $CH_4$ concentration in the $CH_4/C_2H_4/H_2$ feed mixture increases and thus $H_2$ concentration decreases. The $C_2H_4$ concentration increased to 2.84%, 3.25% and 3.53% when the $H_2$ membrane separator had removal efficiencies of 40%, 70% and 100%, respectively. Compared to the number of cycles in FIG. 8A, —50% $CH_4$ conversion can be achieved in a smaller number of cycles for the higher $H_2$ removal efficiencies of FIGS. 8B-8D. However, in contrast to FIG. 8A, the feed flow rate of FIGS. 8B-8D decrease with increasing cycle number. Product yield is limited by $H_2$ separation flux. By increasing the temperature, the $H_2$ flux will increase, and thus product yield will also increase for each cycle. As noted above, such higher temperature operations can be enabled by the use of a sweep gas comprising $O_2$ or an oxygen-containing compound, in particular, where back-diffusion of oxygen avoids, or at least reduces, coking of the membrane.

The feed stream with the same composition and flow rate as determined above for the DNMC reactor in Section 3.2.1 was tested over the Fe@SiO$_2$ catalyst in the DNMC reactor. FIGS. 9A-9D show the $CH_4$ conversion and product selectivity at different cycle numbers and different $H_2$ removal efficiency conditions. At 10% $H_2$ removal efficiency in each cycle, $CH_4$ conversion decreased as the cycle number increased, as shown in FIG. 9A. Two different phenomena can govern the effects of the $CH_4$ conversion trend. From the second cycle onward, $C_2$ and $H_2$ were included in the feed gas as a result of the DNMC reaction from the previous cycle, which will affect the equilibrium $CH_4$ conversion. According to the Le Châtelier's principle, the inclusion of $H_2$ will shift the equilibrium to the reactant side lowering the $CH_4$ conversion. From the feed composition at each cycle (FIG. 8A), an increase in $H_2$ concentration of the feed gas was observed, which agreed with the decreasing trend of the $CH_4$ conversion. In addition, from FIG. 8A, the total flow rates of the subsequent cycles were slightly higher than the first cycle, which means higher space velocities for the DNMC reaction that in turn leads to lower $CH_4$ conversion. As for the selectivity, the product selectivity shifted toward lighter products as the cycle number increased, due to the addition of $H_2$ in the feed of the subsequent cycles, which shifts the overall equilibrium of the DNMC reaction to lighter hydrocarbons.

Figure 9B:
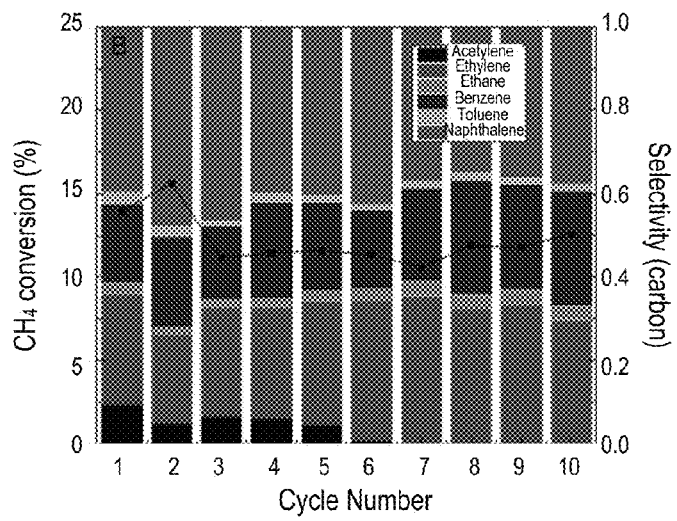
Figure 9C:
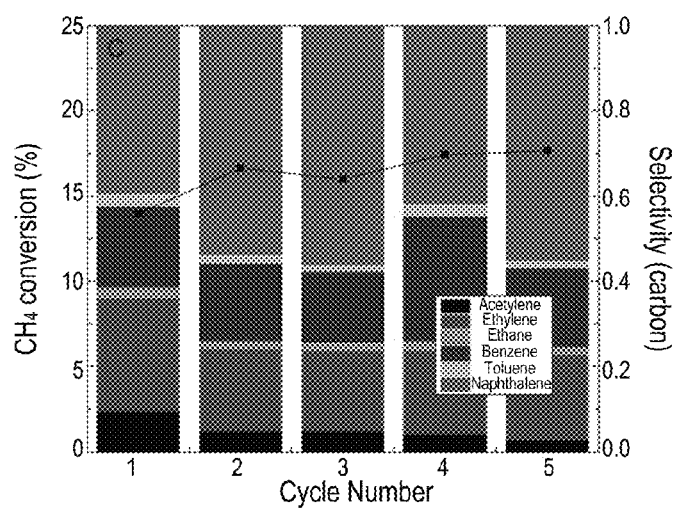
Figure 9D:
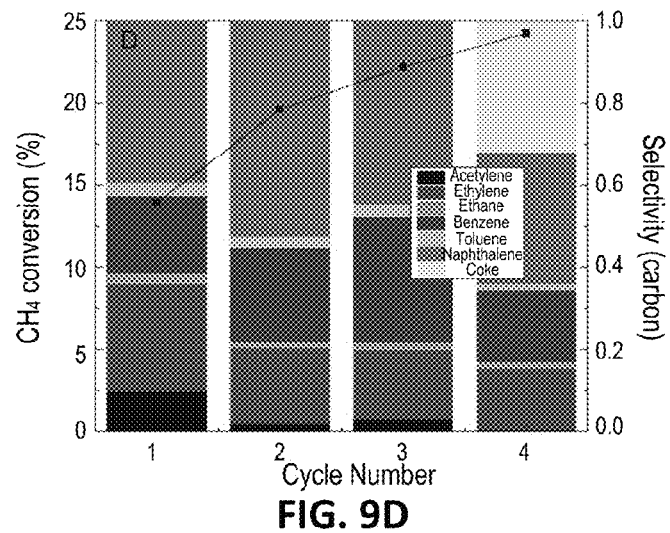
Figure 10A:
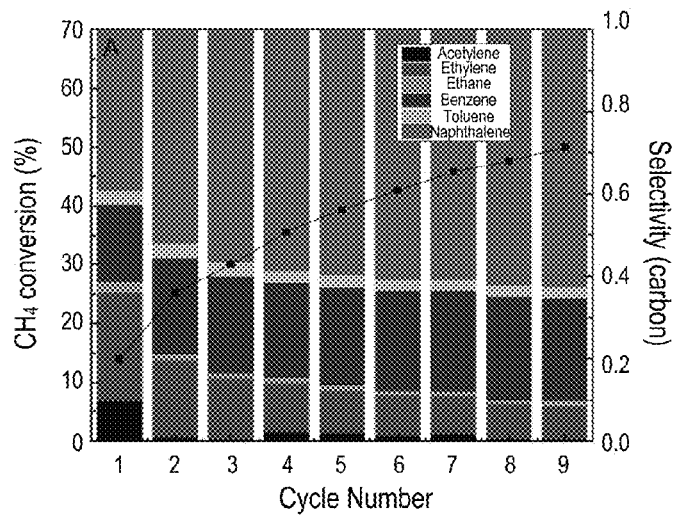
FIGS. 10A-10D are graphs of overall methane conversion and product selectivity at different cycle numbers for $H_2$ removal efficiencies by the hydrogen separator of 10% $H_2$ removal, 40% $H_2$ removal, 70% $H_2$ removal, and 100% $H_2$ removal, respectively.
Figure 10B:
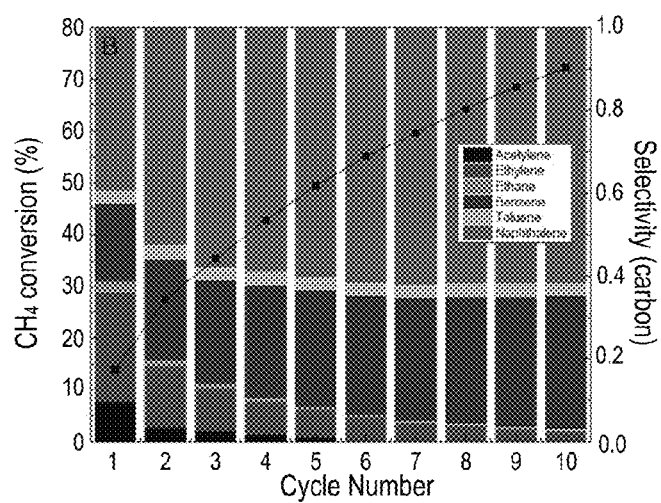
Figure 10C:
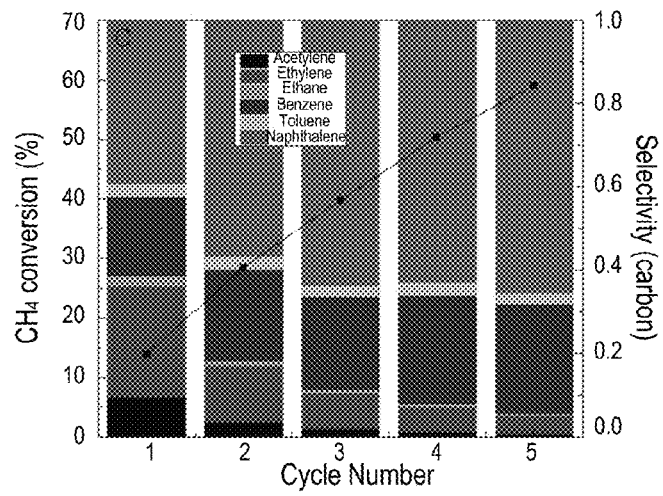
Figure 10D:
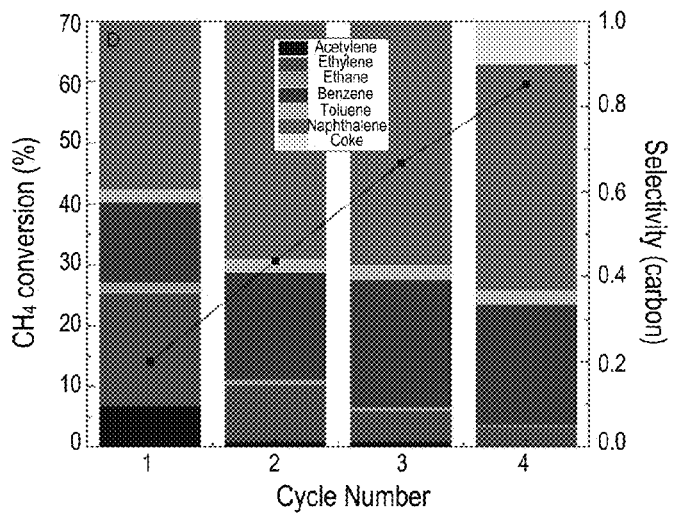

Based on the feed flow rate and composition analysis of FIGS. 8B-8D, the aromatics liquid production from DMNC reaction can be enhanced significantly if the $H_2$ removal efficiency is further improved. Again, the $H_2$ flux can be increased by increasing the temperature, and such higher temperature operations can be enabled by the use of a sweep gas comprising $O_2$ or an oxygen-containing compound to avoid, or at least reduce, coking of the membrane. FIG. 8B shows the performance of the $CH_4$ reactor at 40% $H_2$ removal in the $H_2$ separator in each cycle. First, the $H_2$ content leftover in the feed of the subsequent cycles (FIG. 8B) were less compared to the case of the 10% $H_2$ removal. However, the amount of $H_2$ in this feed stream (up to ~30%) should still lead to lower $CH_4$ conversion, and shift product selectivity towards lighter hydrocarbons. Second, the overall gas feed flow rates dropped significantly (up to ~50%), which led to lower space velocities for the DNMC reaction. Lower space velocities of DNMC should lead to higher $CH_4$ conversion and shift the product selectivity toward larger hydrocarbons. These two effects seemed to balance each other out at the case of 40% $H_2$ removal efficiency. As shown in FIG. 9B, a relatively stable $CH_4$ conversion and product selectivity were achieved in this case in each reaction cycle.

At significant levels of $H_2$ removal efficiencies of 70% (FIG. 9C) and 100% (FIG. 9D), the effects of lowering DNMC reaction space velocities dominate over the inclusion of $H_2$ in the subsequent cycles. Therefore, the $CH_4$ conversion increased as the cycle number increased for 70% $H_2$ removal efficiency and 100% $H_2$ removal efficiency. In addition, the product selectivity shifted toward larger aromatic hydrocarbons (liquid). Too high of a reduction in the DMNC space velocities led to coke formation, which was demonstrated at the fourth cycle of the reaction with 100% $H_2$ removal in FIG. 9D.

Based on the above-described separate performance evaluations of the DNMC reactor and the $H_2$ membrane separator, the overall performance of the gas recycle system (integrating the DNMC reactor and $H_2$ membrane separator) can be evaluated to understand the overall $CH_4$ conversion, product selectivity, and yields. In particular, FIGS. 10A-10D show the overall $CH_4$ conversion and product selectivity at different levels of $H_2$ removal efficiency, with $H_2$ separation performed at 1073 K using a single $H_2$ permeable membrane). As is apparent from FIGS. 10A-10D, all of the $H_2$ removal levels showed similar trends in methane conversion and product selectivity. As the number of cycles increased, the overall $CH_4$ conversion increased, with the overall $CH_4$ conversion reaching over 70% and potentially higher. The product selectivity also exhibited the same trend. As the number of cycles increased, the product selectivity shifted toward larger aromatic hydrocarbons (liquid), with the liquid portion of the products reaching over 95%. As the amount of $H_2$ removal increases, it takes a fewer number of cycles to reach the same level of $CH_4$ conversion, since the equilibrium conversion is enhanced by shifting toward the product side according to the Le Châtelier's principle.

Figure 11:
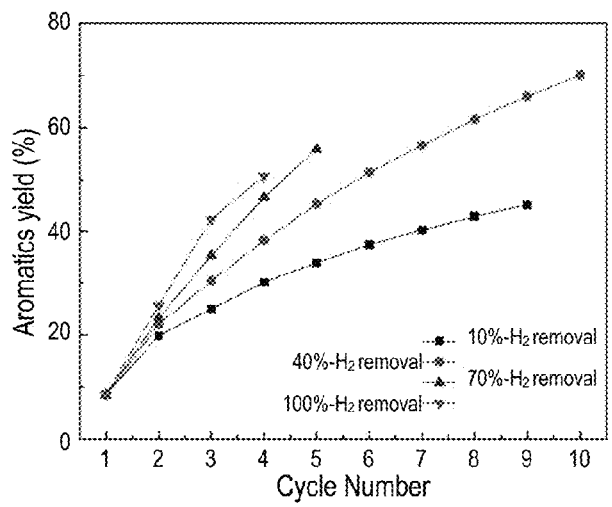
FIG. 11 is a graph of overall aromatic liquid yield from DNMC at different cycle numbers for $H_2$ removal efficiencies by the hydrogen separator of 10% $H_2$ removal, 40% $H_2$ removal, 70% $H_2$ removal, and 100% $H_2$ removal, respectively.

FIG. 11 shows the overall aromatics yields at different $H_2$ removal efficiencies. In the experimental setup comprising the DNMC reactor and the $H_2$ separator using a single $SrCe_{0.7}Zr_{0.2}Eu_{0.1}O_{3\delta}$ membrane tube, the yield of aromatics was >40% after nine cycles for 10% $H_2$ removal, as shown in FIG. 11. With higher $H_2$ removal efficiencies, the system has the potential to reach even higher aromatics yield. For example, at 40% $H_2$ removal, the aromatics yield can reach over 70%. Comparing the aromatics yields of the system with different $H_2$ removal efficiencies clearly shows that the higher $H_2$ removal capability of the $H_2$ separator leads to higher aromatics yield, since removal of H shifts the equilibrium to the product side, which increases the equilibrium $CH_4$ conversion.

Autothermal Membrane Reactor Operation

To test performance of an autothermal reactor (e.g., having a setup similar to heat-exchange reactor 290 in FIG. 2E), a DNMC reaction was run at atmospheric pressure in both a fixed-bed reactor (without $H_2$ permeation, similar to reactor 230 in FIG. 2B) and a tubular membrane reactor (with $H_2$ permeation). In the experiments, 0.375 g of Fe@SiO$_2$ catalyst was loaded at the center of the reactor and then heated to the desired temperature in pure Ar at the rate of 20 mL/min. After the reaction gas mixture (90% $CH_4$ and 10% Ar) was introduced, the reaction was run at a temperature range of 1253-1303 K and at a feed gas space velocity of 3200 mL/(g-h). During the reaction in the heat-exchange $H_2$-permeable membrane reactor, a mixture of 20 mol % $O_2$ balanced by He was introduced as the sweep gas. The concentration of $O_2$ in the sweep gas is similar to that of air, but He was used instead of $N_2$ in the experiments due to the high-sensitivity of flame ionization detector (FID) and thermal conductivity detector (TCD) caused by He carrier gas in the gas chromatography. The $CH_4$ reactant was introduced through the inner tube in the top center section of the heat-exchange $H_2$-permeable reactor and the $C_{2+}$ products exited through the catalyst bed in the reactor. The outer annular region of the membrane reactor was exposed to the $O_2$/He sweep gas to carry and react with the permeated $H_2$ away from the reactor system. The effluent gases from the feed side and the sweep side were analyzed on-line by a gas chromatographer (Agilent 6890). Transfer lines were maintained at temperatures greater than 473 K by resistive heating to prevent product condensation.

Figure 12A:
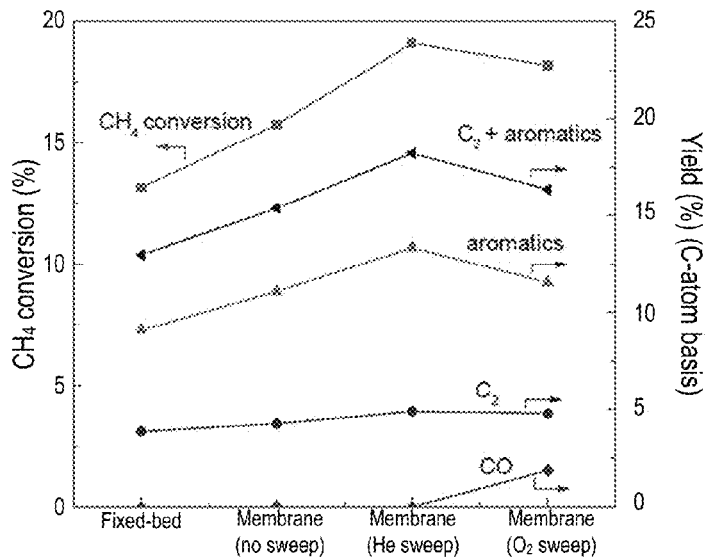
FIG. 12A is a graph of methane conversion and product yield for a fixed-bed reactor with Fe@$SiO_2$ catalyst and for a membrane reactor with different sweep gases.
Figure 12B:
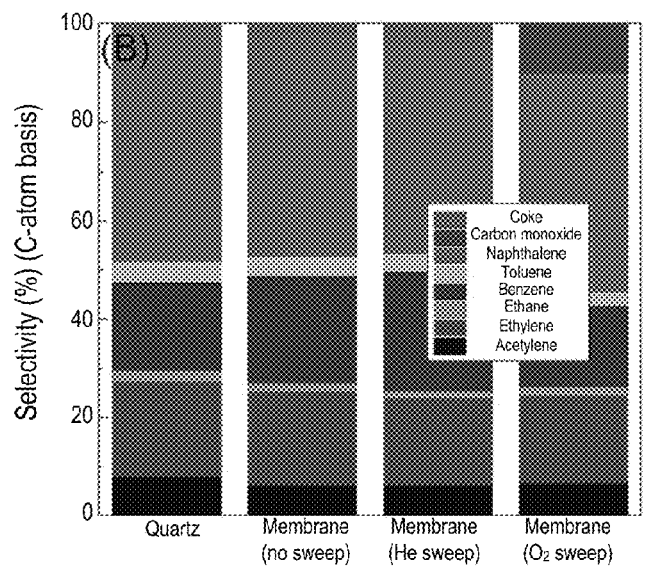
FIG. 12B is a graph of product selectivity for a fixed-bed reactor with Fe@$SiO_2$ catalyst and for a membrane reactor with different sweep gases.

FIGS. 12A-12B show the effects of different sweep gas on the DNMC reaction, which is on the inside of the heat-exchange $H_2$-permeable membrane reactor. As a reference, a control experiment was performed within a fixed-bed reactor that is made of a quartz tube. FIG. 12A shows an increase in $CH_4$ conversion when comparing the fixed-bed reactor (without $H_2$ removal) to the membrane rector with or without the sweep gas flow. Without a sweep gas, $CH_4$ conversion in the membrane reactor was slightly higher compared to the fixed-bed reactor, which is due to activation of methane by the membrane material itself. A control experiment was done by placing the $SrCe_{0.7}Zr_{0.2}Eu_{0.1}O_{3\delta}$ oxide powder in the fixed-bed reactor, which showed the methane conversion with plenty (>50% selectivity) of coke formation at the tested DNMC reaction conditions. The higher coke selectivity of DNMC in the membrane reactor than that of the fixed bed reactor in the absence of any sweep gas, as shown in FIG. 12B, also confirmed the activation of methane into coke by the membrane material itself. By using the sweep gas to simultaneously remove the permeated $H_2$ from the membrane reactor, the reaction is shifted to the product side which increases the $CH_4$ conversion in accordance with Le Châtelier's principle. Therefore, the $H_2$-permeable membrane reactor in the presence of He-only or $O_2$/He sweep gas showed higher $CH_4$ conversion than that of the fixed-bed reactor, as shown in FIG. 12A. When $O_2$ is present in the sweep gas, the $CH_4$ conversion was slightly decreased, which can be attributed to the sacrifice of $H_2$ permeation by back diffusion of $O_2$ in the $SrCe_{0.7}Zr_{0.2}Eu_{0.1}O_{3\delta}$ membrane since CO product is formed in this condition. The product yields, especially the aromatics yield, in all the DNMC test conditions follow the same trend of $CH_4$ conversions.

FIG. 12B compares the product selectivity in DNMC reaction in the fixed-bed and membrane reactors with different sweep gas conditions. When compared to the fixed-bed reactor, the membrane reactor without sweep gas flow showed a slight decrease in $C_2$ selectivity, and a slight increase in both benzene and coke selectivities. Adding an He-only sweep gas in the membrane reactor further shifted the $C_2$ and benzene/coke to lower and higher selectivities, respectively. When $O_2$ was present in the sweep gas, the $C_2$ selectivity kept similar to that of He only sweep gas condition, but the benzene and coke selectivities were decreased. More importantly, coke was not produced, and CO product was formed instead. Therefore, the disclosed membrane reactor systems can have both long-term stability and low-carbon efficiency constraints, for example, by completely eliminating the coke formation and having >90% carbon efficiency.

The formation of CO in the DNMC reaction in the heat-exchange $H_2$-permeable membrane reactor can be attributed to the fact that the MIEC $SrCe_{0.7}Zr_{0.2}Eu_{0.1}O_{3\delta}$ membrane material can co-permeate both $H_2$ and $O_2$ gases (e.g., via respective ions thereof). In particular, the back diffusion of $O_2$ from the $O_2$/He sweep gas across the membrane into the DNMC reaction volume can oxidize any carbon deposition resulting from the DNMC reaction into CO, and thereby eliminate, or at least reduce, coke formation. Concurrently, when $O_2$ is used in the sweep gas, the ambipolar conductivity of the $SrCe_{0.7}Zr_{0.2}Eu_{0.1}O_{3-\delta}$ membrane may decrease, which can lead to a decrease in the rate of $H_2$ permeation, and therefore lower $CH_4$ conversion. On the other hand, when permeated $H_2$ is readily combusted by $O_2$ in the sweep gas, there is an increase in the $H_2$ partial pressure difference across both sides of the membrane, which can lead to an increase in $H_2$ permeation, and therefore higher $CH_4$ conversion. As shown in FIG. 12A, a slight decrease in overall $CH_4$ conversion is observed when switching from He-only to $O_2$/He sweep gas, suggesting that the trade-off between effects of the decrease in ambipolar conductivity and effects of the increase in $H_2$ partial pressure gradient is dominated by the former property in the tested conditions.

Figure 13A:
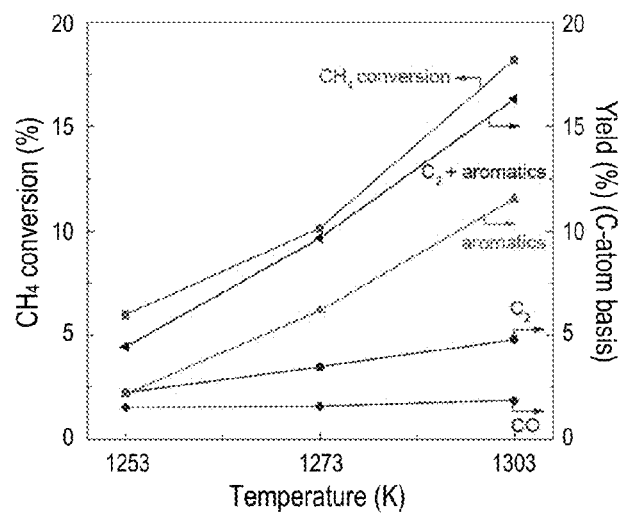
FIG. 13A is a graph of methane conversion and product yield from DNMC by a heat-exchange $H_2$-permeable membrane reactor as a function of temperature.
Figure 13B:
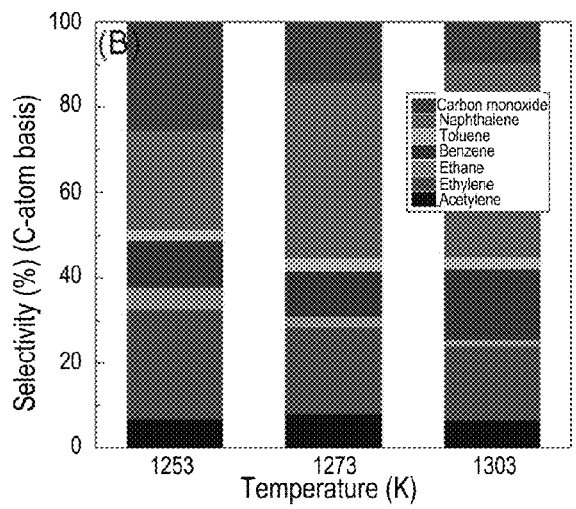
FIG. 13B is a graph of product selectivity from DNMC by the heat-exchange $H_2$-permeable membrane reactor as a function of temperature.

The effects of reaction temperature on methane conversion, product yield and selectivity, $H_2$ production and permeation, as well as heat requirement for DNMC and heat release from combustion of $H_2$ permeate were studied, and the results are summarized in FIGS. 13A-13D. An increase in $CH_4$ conversion with increasing temperature is observed in FIG. 13A, which is due to the endothermic nature of the DNMC reaction. The product yields also increases with increasing reaction temperature. In particular, the aromatics yield increases significantly and $C_2$ hydrocarbon yield increased moderately, while CO only exhibited a slight increase, as shown in FIG. 13A. FIG. 13B shows the product selectivity versus reaction temperature in DNMC in the heat-exchange $H_2$-permeable membrane reactor. As the temperature is increased, the product selectivity shifts from smaller $C_2$ products to aromatics. This trend corresponds to the thermodynamic nature of the DNMC reaction, which means that high reaction temperature and high $CH_4$ conversion favor heavy product formation. The CO selectivity, however, exhibited an opposite trend with increasing reaction temperature. Regardless, there was no coke formation at any of the tested temperature conditions.

Figure 13C:
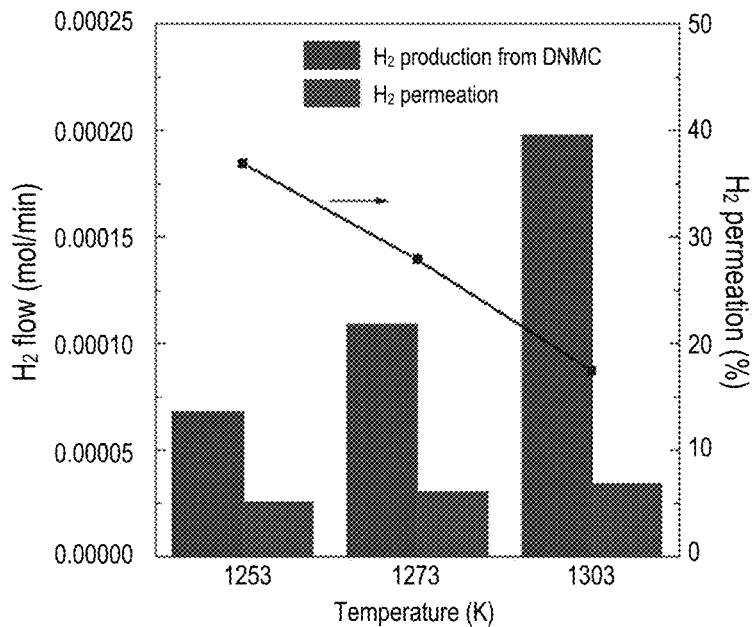
FIG. 13C is a graph of $H_2$ production and permeation, and $H_2$ removal percentage in the DNMC by the heat-exchange $H_2$-permeable membrane reactor as a function of temperature.

FIG. 13C shows the rates of $H_2$ generation from DNMC and $H_2$ permeation through the MIEC membrane at the three tested temperatures (1253 K, 1273 K, and 1303 K). The $H_2$ production rate was calculated from the carbon balance in the DNMC reaction, while the $H_2$ permeation rate was evaluated on the basis of hydrogen balance in both DNMC and $H_2$ combustion reactions. When the reaction temperature was increased (e.g., from 1253 K, or 1273 K, to 1303 K), a significant increase in the $H_2$ production rate was observed. The $H_2$ permeation rate through the membrane increased slightly with the reaction temperature. Therefore, the percentages of $H_2$ removal were calculated to be 36.9%, 27.9% and 17.5% at 1253 K, 1273 K, and 1303 K, respectively. Since $O_2$ content is in excess compared to $H_2$ permeate in the sweep gas side, the $H_2$ permeate was completely consumed by the combustion reaction outside of the MIEC membrane tube.

From the oxygen balance in the membrane reactor, the $O_2$ conversions were found to be 7.7%, 9.3% and 10.6% at the reaction temperatures of 1253 K, 1273 K, and 1303 K, in sequence. Thus, the $O_2$ residue in the sweep gas decreases with increasing reaction temperature. As noted above, the back diffusion of $O_2$ from the $O_2$/He sweep gas (through the MIEC membrane into the DNMC reaction volume) was responsible for CO formation. According to the Wagner Equation, the $O_2$ permeation should increase with temperature, but a decrease in $O_2$ concentration on the sweep side of the membrane can lead to lower $O_2$ permeation. The interaction between these two opposing effects can offset each other, such that the CO yield at different reaction temperatures remains about the same, as shown in FIG. 13A.

Figure 13D:
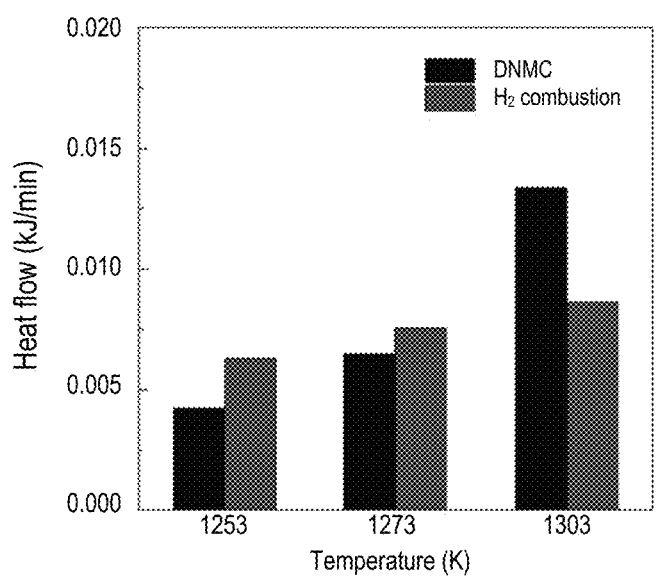
FIG. 13D is a graph comparing heat requirement for DNMC and heat released from combustion of $H_2$ permeate for different temperatures.

As shown in FIG. 13B, the significant increase in $C_{2+}$ yields resulted in a decrease in CO selectivity with increasing reaction temperature. The material balance analyses in FIGS. 13A-13C, together with heat of reactions for both DNMC and $H_2$ combustion, enables the autothermality analysis for the $H_2$-permeable membrane reactor. FIG. 13D compares the heat requirement for DMNC and the heat release from the combustion of $H_2$ permeate at 1253 K, 1273 K, and 1303 K. At the lower temperature (1253 K), the heat released from $H_2$ combustion was higher than that of heat requirement for DNMC reaction. At the middle temperature (1273 K), the heat released from $H_2$ combustion and the heat requirement for DNMC reaction are almost identical to each other. When the reaction temperature is increased to the higher temperature (1303 K), the heat released from $H_2$ combustion is not enough to match the heat requirement for the DNMC reaction, which is caused by the low $H_2$ removal (17.5%). Overall, the results confirm that the autothermality of DNMC in the heat-exchange $H_2$-permeable membrane reactor can be achieved at ~30% $H_2$ removal from the DNMC reaction. Ambipolar conductivity of the MIEC $SrCe_{0.7}Zr_{0.2}Eu_{0.1}O_{3-\delta}$ membrane can be improved in order to reach the balance between the endothermic heat requirement of DNMC reaction and the heat released from combustion of $H_2$ permeate at high reaction temperatures.

Figure 14A:
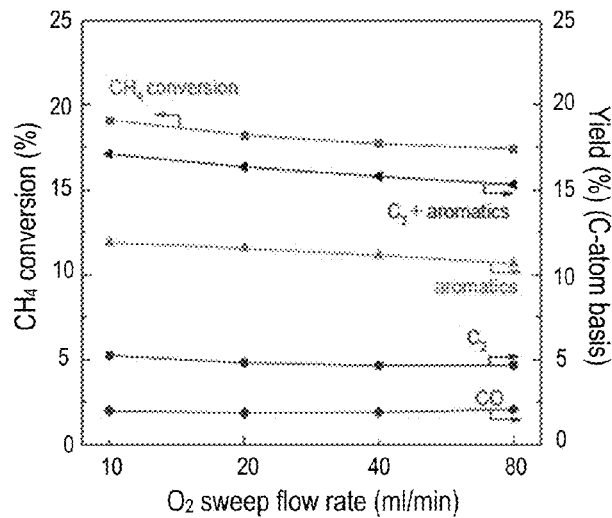
FIGS. 14A, 14D, and 14G are graphs of methane conversion and product yield as a function of $O_2$ sweep flow rate during DNMC by the heat-exchange $H_2$-permeable membrane reactor at 1303 K, 1273 K, and 1253 K, respectively.
Figure 14B:
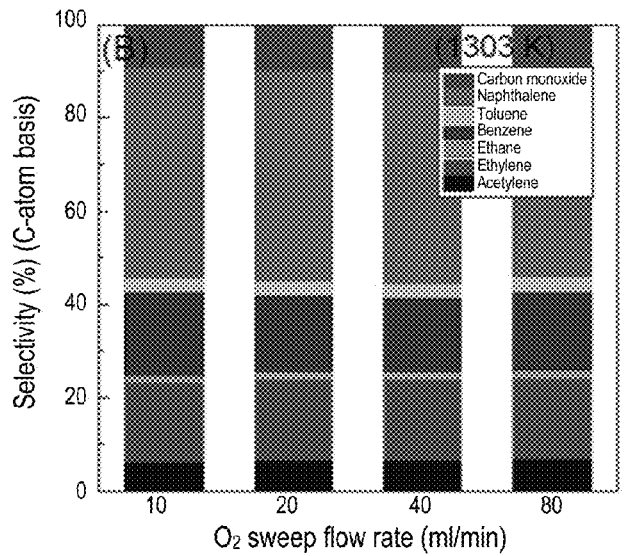
FIGS. 14B, 14E, and 14H are graphs of product selectivity as a function of $O_2$ sweep flow rate during DNMC by the heat-exchange $H_2$-permeable membrane reactor at 1303 K, 1273 K, and 1253 K, respectively.

To study tunability of autothermality of DNMC in the heat-exchange $H_2$-permeable membrane reactor, the effects of $O_2$ sweep gas flow rates on the DNMC reaction and heat generation/consumption in both DNMC and $H_2$ combustion reactions were measured. FIGS. 14A-14I show the $CH_4$ conversion, product yield and selectivity, and heat release by $H_2$ combustion and heat requirement for DNMC as a function of sweep gas flow rate (10-80 mL/min) at 1253 K, 1273K, and 1303 K. At 1303 K, the increasing $O_2$ sweep gas flow rate led to a slight decrease in $CH_4$ conversion and thus $C_{2+}$ product yield, as shown in FIG. 14A. When the reaction temperature is lower (e.g., 1253 K), $CH_4$ conversion increased slightly and then decreased with increasing sweep gas flow rate, as shown in FIG. 14G. At the reaction temperature of 1273 K, the changing trend of $CH_4$ conversion and $C_{2+}$ product yield with respect to sweep gas flow rate stayed between that of 1253 and 1303 K, which showed a decrease and then a plateau with increasing $O_2$ sweep flow rate, as shown in FIG. 14D. Overall, there was no obvious change in the $CH_4$ conversions and $C_{2+}$ product yields with respect to the sweep gas flow rates. FIGS. 14B, 14E, and 14H show the product selectivity as a function of $O_2$ sweep gas flow rate at 1303 K, 1273 K, and 1253 K, respectively. With increasing $O_2$ sweep gas flow rate, the CO selectivity increased, accompanied with reduction in aromatics selectivity.

The increase in $O_2$ sweep gas flow rate could cause two competing phenomena in the heat-exchange membrane reactor that can influence the $CH_4$ conversion. The increasing $O_2$ sweep flow rate can increase $O_2$ exposure to the $SrCe_{0.7}Zr_{0.2}Eu_{0.1}O_{3-\delta}$ membrane per unit time, and thus the surface exchange rate of $O_2$ with the membrane material. This can have a negative effect on the ambipolar conductivity of the membrane, which leads to a decrease in the flux of the $H_2$ permeation and therefore lowers $CH_4$ conversion. At the same time, the permeated $H_2$ is combusted at a higher rate with increasing $O_2$ sweep gas flow rate, which leads to an increase in $H_2$ partial pressure gradient and an increase in $CH_4$ conversion. As indicated by the decrease in $CH_4$ conversion with increasing $O_2$ sweep flow rate, a decrease in the ambipolar conductivity of the $SrCe_{0.7}Zr_{0.2}Eu_{0.1}O_{3-\delta}$ membrane dominates the overall performance, even though it is somewhat offset by the increase in $H_2$ partial pressure gradient.

Figure 14C:
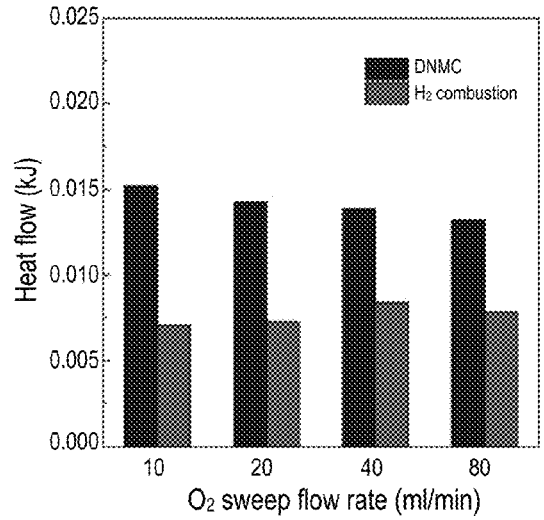
FIGS. 14C, 14F, and 14I are graphs of heat requirement for DNMC and heat release from combustion of $H_2$ permeate as a function of $O_2$ sweep flow rate during DNMC by the heat-exchange $H_2$-permeable membrane reactor at 1303 K, 1273 K, and 1253 K, respectively.
Figure 14D:
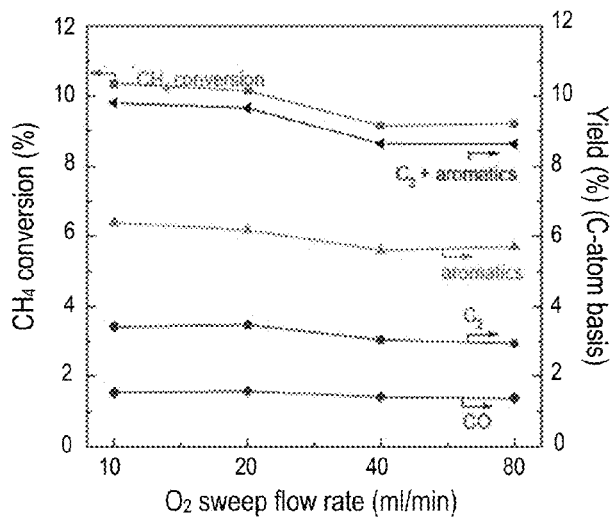
Figure 14E:
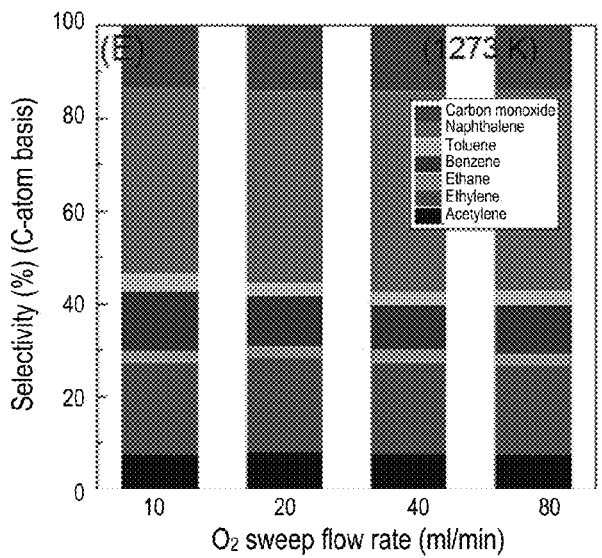
Figure 14F:
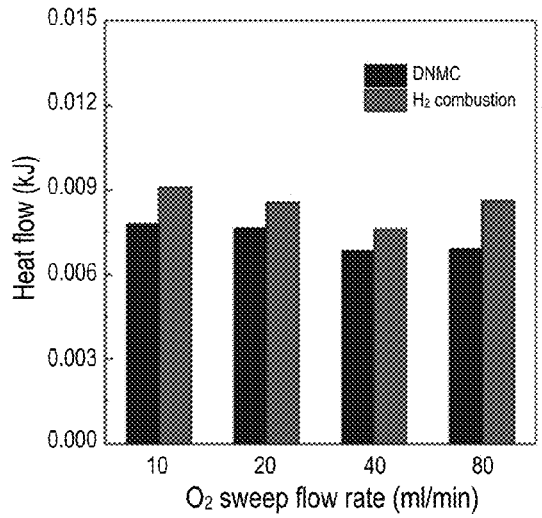
Figure 14G:
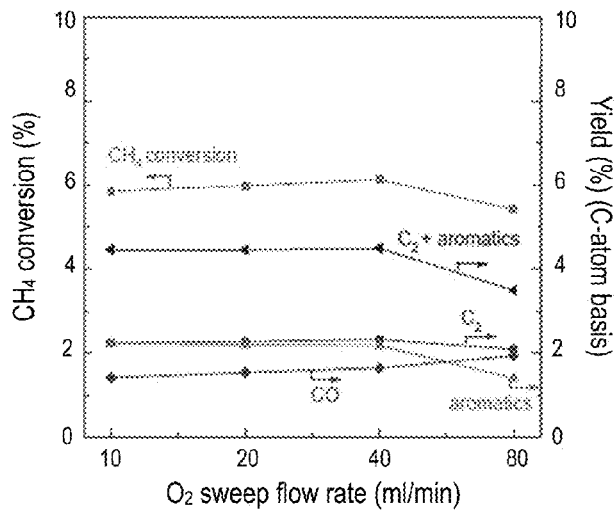
Figure 14H:
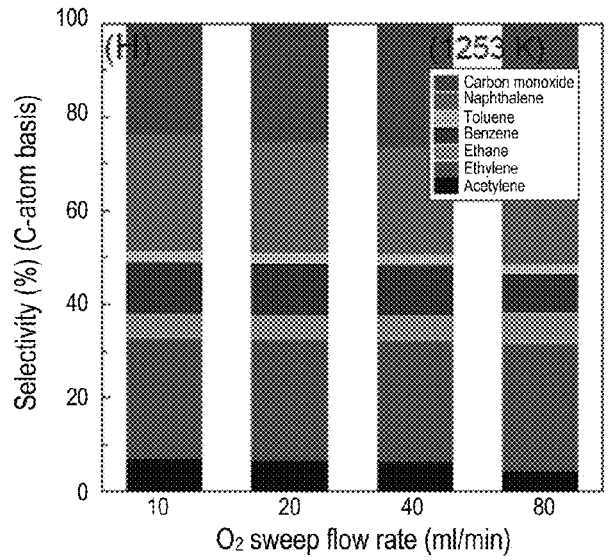
Figure 14I:
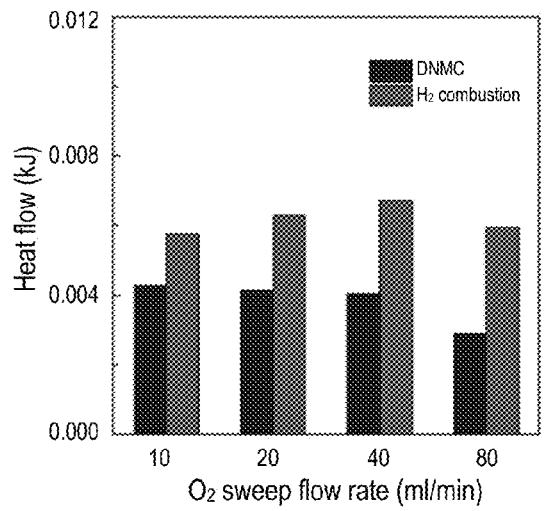

FIGS. 14C, 14F, and 14I compare the heat requirement for DMNC and heat release from the combustion of permeated $H_2$ at different $O_2$ sweep flow rates. At 1303 K, the heat released from the combustion of permeated $H_2$ was not enough to supply heat for the DNMC reaction, even with high $O_2$ sweep gas flow rate, as shown in FIG. 14C. This was due to the insufficient $H_2$ flux across the membrane, compared to the $H_2$ generation from the DNMC reaction. In addition, the heat requirement for DNMC decreased and the heat release from $H_2$ combustions increased as the $O_2$ sweep flow rate increased from 10 to 40 mL/min. The former case was caused by the decreasing $CH_4$ conversion, while the latter was caused by the high $H_2$ permeation and combustion. When the $O_2$ sweep flow rate was very high (e.g., 80 mL/min), the heat release from $H_2$ combustion was decreased slightly, which may have been caused by the deterioration of ambipolar conductivity of the membrane under very high $O_2$ sweep gas flow conditions.

At 1273 K, the overall $CH_4$ conversion decreased when compared to 1303 K, and therefore the heat requirement from the DNMC side was reduced, as shown in FIG. 14F. The results showed that the heat released from the combustion of permeated $H_2$ matched the required heat input for the DNMC reaction, which meant that autothermal operation was achieved in all the $O_2$ sweep gas flow rates. When the reaction temperature was reduced to 1253 K, the heat release from combustion of $H_2$ permeate overcomes that required by DNMC reaction, as shown in FIG. 14I. This phenomenon was maintained regardless of the $O_2$ sweep flow rate. Overall, the results show that the flow rate of $O_2$ sweep gas does not modulate the autothermality of DNMC.

Figure 15A:
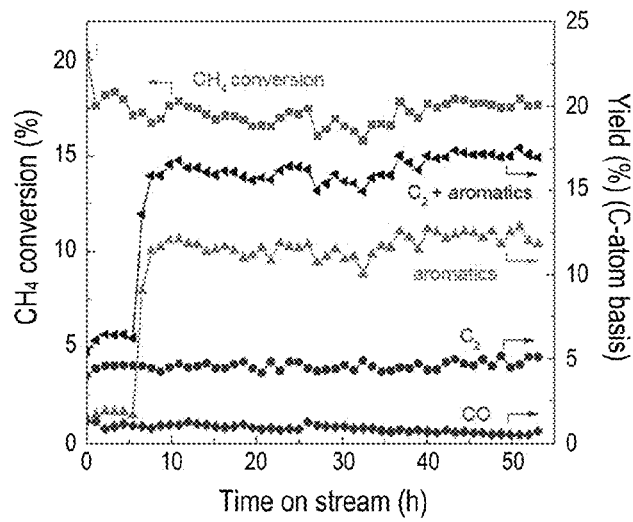
FIG. 15A is a graph of methane conversion and product yield for DNMC by the heat-exchange $H_2$-permeable membrane reactor at 1303 K as a function of time on stream.

The stability of the heat-exchange $H_2$-permeable membrane reactor was tested by running DNMC at 1303 K for 50 hours while flowing the $O_2$ sweep gas, the results of which stability test are shown in FIG. 15A. An induction period of ~5 hours was observed in the initial state of the reaction where the aromatics yield was low. After the induction period, the membrane reactor reached a stable performance, where the $CH_4$ conversion remained at ~18.0%. The product yields of $C_2$ products, aromatics, $C_{2+}$ products (i.e., $C_2$+aromatics), and CO were stable at approximately 4.6%, 11.9%, 16.5%, and 0.7%, respectively. The CO formation, due to back diffusion of oxygen from the sweep side into the DNMC reaction volume, limited coke accumulation in the membrane reactor, and thus maintained the long-term stability of the reactor. The CO selectivity was approximately 3.3%, and almost 97% carbon conversion efficiency was obtained in the studied conditions.

Figure 15B:
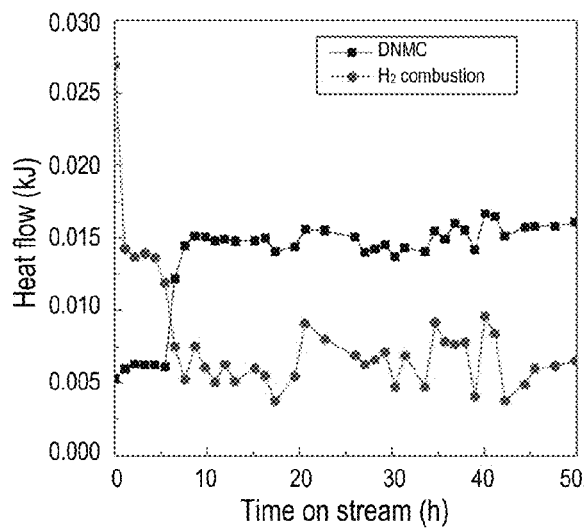
FIG. 15B is a graph of heat requirement for DNMC and heat release from combustion of $H_2$ permeate during DNMC by the heat-exchange $H_2$-permeable membrane reactor at 1303 K as a function of time on stream.

FIG. 15B shows the heat requirement for DNMC and heat release from combustion of $H_2$ permeate on opposite sides of the $SrCe_{0.7}Zr_{0.2}Eu_{0.1}O_{3-\delta}$ membrane. After the induction period, the heat requirement for DNMC and the heat release from the $H_2$ combustion were stable throughout the long-term test. The selected reaction temperature (1303 K) in the long-term stability tests was the harshest condition among all the tested reaction conditions, and thus it is expected that the heat-exchange $H_2$-permeable membrane reactor can maintain autothermality and have stable performance under lower reaction temperatures (e.g., 1253 K or 1273 K).

To further examine feasibility of the autothermal operation of DNMC process in the heat-exchange membrane reactor at an industrial scale, Aspen Plus® was used to simulate the scenario on the basis of the experimental results at 1273 K, where ~30% of $H_2$ was removed from the DNMC reaction and was completely combusted by the sweep gas (e.g., $O_2$ in air). At 1273 K, the total heat requirement for the entire process was found to be 2,360,715 kJ/h, while the total heat released was found to be −2,408,618 kJ/h, resulting in a net −47,903 kJ/h of heat released overall. Furthermore, the simulation results of the heat exchanger demonstrate that the heat released from the cooling of both the DNMC product stream and the $H_2$ combustion stream are sufficient to heat the DNMC and $H_2$ combustion feed streams. The results of the Aspen Plus® simulation further showed that autothermal operation was feasible for the scaled-up DNMC process, indicating the potential for autothermality of DNMC operation under realistic conditions.

Figure 16:
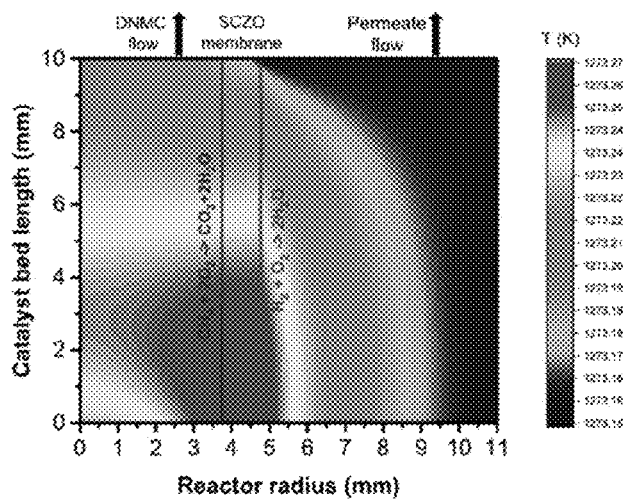
FIG. 16 is a graph illustrating a two-dimensional temperature profile of the heat-exchange $H_2$-permeable membrane reactor during operation thereof at 1273 K.

To supplement the Aspen Plus® simulation, additional COMSOL simulations were performed to understand the effects of gas flow velocities, $CH_4$ concentration, and temperature profiles of the membrane reactor on the performance of the DNMC reaction. In particular, a COMSOL 2D axisymmetric model of the DNMC reaction, coupled with the $SrCe_{0.7}Zr_{0.2}Eu_{0.1}O_{3-\delta}$ membrane reactor with $O_2$ sweep gas, was generated. The COMSOL simulation was conducted on the catalyst bed region of the membrane reactor for both DNMC channel and hydrogen combustion side. The gas velocities fell near the reactor wall and the membrane walls (i.e., in both DNMC and $H_2$ combustion sides) due to the no-slip boundary conditions. The $CH_4$ concentration fell from the entrance to the exit of the catalyst bed due to the reaction of $CH_4$ in the DNMC catalyst bed. From the center to the wall of the membrane reactor, the $CH_4$ concentration decreased gradually. The rapid decrease in $CH_4$ concentration close to the reactor wall was due to the low gas velocity, which in turn limited the convection of fresh reactant to that wall. FIG. 16 shows the temperature profile of the DNMC catalyst bed inside the membrane reactor. As shown in FIG. 16, changes in temperature were insignificant, as the heat provided by the furnace played an important role in maintaining the reactor at 1273 K, and the maximum temperature difference was only ~0.2 K. The outer wall temperature was set to 1273 K, which strongly affected the temperature distribution. The heat generated from $H_2$ combustion was insignificant, and it did not affect the overall temperature. However, it was enough energy to balance out the heat required by the DNMC reaction.

CONCLUSION

Any of the features illustrated or described herein, for example, with respect to FIGS. 1A-16, can be combined with any other feature illustrated or described herein, for example, with respect to FIGS. 1A-16 to provide systems, devices, methods, and embodiments not otherwise illustrated or specifically described herein. For example, any of the reactors illustrated in FIGS. 2C-2E (e.g., modified to include an appropriate catalyst) and/or any of the reactors illustrated in FIGS. 2B and 2E can be used for reactor 107 in FIG. 1A, reactor 106 in FIG. 1B, any of reactors 107, 156 in FIG. 1C, any of reactors 184, 186 in FIG. 1D, reactor 206 in FIG. 2A, or reactor 410 in FIG. 4. In another example, any of the reactors illustrated in FIGS. 2C-2E (e.g., with or without an appropriate catalyst) can be used for reactor 127 in FIG. 1A, reactor 126 in FIG. 1B, any of reactors 156, 127 in FIG. 1C, any of reactors 194, 196 in FIG. 1D, separator 216 in FIG. 2A, or membrane separator 430 in FIG. 4.

All features described herein are independent of one another and, except where structurally impossible, can be used in combination with any other feature described herein. In view of the many possible embodiments to which the principles of the disclosed technology may be applied, it should be recognized that the illustrated embodiments are only examples and should not be taken as limiting the scope of the disclosed technology. Rather, the scope is defined by the following claims. We therefore claim all that comes within the scope and spirit of these claims.

The invention claimed is:

1. A methane conversion system comprising:
a first membrane reactor comprising a first gas flow volume, a second gas flow volume, and a first membrane separating the first gas flow volume from the second gas flow volume, the first gas flow volume having a first catalyst therein;
a first gas supply coupled to the second gas flow volume and constructed to provide a first sweep gas to the second gas flow volume, the first sweep gas comprising $O_2$ or an oxygen-containing compound;
an aromatics separation device connected to receive a first processed stream from the first gas flow volume;
a second membrane reactor comprising a third gas flow volume, a fourth gas flow volume, and a second membrane separating the third gas flow volume from the fourth gas flow volume, the third gas flow volume having a second catalyst therein;
a second gas supply coupled to the fourth gas flow volume and constructed to provide a second sweep gas to the fourth gas flow volume, the second sweep gas comprising $O_2$ or an oxygen-containing compound; and
a recycle line comprising one or more fluid conduits, the first gas flow volume of the first membrane reactor being connected to receive a recycle stream from the third gas flow volume of the second membrane reactor via the recycle line,
wherein the first reactor is constructed to convert at least some $CH_4$ in an input gas flow stream provided to the first gas flow volume of the first reactor, so as to provide a first processed stream and such that a quantity of $CH_4$ in the first processed stream is less than that in the input gas flow stream, the first processed stream comprising $CH_4$, $C_2$ hydrocarbons, and aromatics,
the $C_2$ hydrocarbons are acetylene ($C_2H_2$), ethylene ($C_2H_4$), ethane ($C_2H_6$), or any combination of the foregoing,
the aromatics are benzene ($C_6H_6$), toluene ($C_7H_8$), naphthalene ($C_{10}H_8$), or any combination of the foregoing,
the first membrane is constructed such that at least some $H_2$ is removed from the first gas flow volume by hydrogen ions permeating through the first membrane into the second gas flow volume and such that oxygen ions permeate through the first membrane from the second gas flow volume into the first gas flow volume so as to reduce coking of the first membrane,
the first reactor is constructed for autothermal operation via an exothermic reaction between the permeated hydrogen in the second gas flow volume and the $O_2$ or oxygen-containing compound in the second gas flow volume,
the aromatics separation device is constructed to remove at least some aromatics from the received first processed stream, so as to provide a second processed stream comprising $CH_4$ and $C_2$ hydrocarbons, and to provide a first output stream comprising the removed at least some aromatics, a quantity of the aromatics in the second processed stream being less than in the first processed stream, the second reactor is constructed to convert at least some $CH_4$ in the second processed stream provided to the third gas flow volume of the second reactor, so as to provide a recycle stream to the recycle line and such that a quantity of $CH_4$ in the recycle stream is less than in the second processed stream, the second processed stream comprising $C_2$ hydrocarbons and aromatics, the second membrane is constructed such that at least some $H_2$ is removed from the third gas flow volume by hydrogen ions permeating through the second membrane into the fourth gas flow volume and such that oxygen ions permeate through the second membrane from the fourth gas flow volume into the third gas flow volume so as to reduce coking of the second membrane, and the second reactor is constructed for autothermal operation via an exothermic reaction between the permeated hydrogen in the fourth gas flow volume and the $O_2$ or oxygen-containing compound in the fourth gas flow volume.

2. The methane conversion system of claim 1, wherein the first catalyst, the second catalyst, or both the first and second catalysts comprise Fe@$SiO_2$.

3. The methane conversion system of claim 1, wherein the first membrane, the second membrane, or both the first and second membranes comprise a perovskite-type oxide having a formula of $M'Ce_{1-x-y}Zr_xM''_yO_{3-\delta}$, where:

M' is a least one of Sr and Ba;

M'' is at least one of Ti, V, Cr, Mn, Fe, Co Ni, Cu, Nb, Mo, W, Pr, Nd, Pm, Sm, Eu, Gd, Tb, Dy, Ho, Er, Tm and Yb;

x is between 0.01 and 0.2, inclusive; and y is between 0.01 and 0.3, inclusive.

4. The methane conversion system of claim 1, further comprising a storage container in fluid communication with the aromatics separation device and constructed to store the removed aromatics therein.

5. The methane conversion system of claim 1, wherein the aromatics separation device comprises a condenser constructed to liquefy the at least some aromatics.

6. A method comprising:

(a) providing an input gas flow stream to a first gas flow volume of a first membrane reactor, the first membrane reactor comprising the first gas flow volume, a second gas flow volume, and a first membrane separating the first gas flow volume from the second gas flow volume, the first gas flow volume having a first catalyst therein;

(b) providing, via a first gas supply, a first sweep gas to the second gas flow volume, the first sweep gas comprising 02 or an oxygen-containing compound;

(c) converting, via the first membrane reactor, at least some at least some $CH_4$ in the input gas flow stream into $C_2$ hydrocarbons, $H_2$, and aromatics, so as to provide a first processed stream comprising $CH_4$, $C_2$ hydrocarbons, $H_2$, and aromatics and such that a quantity of CH4 in the first processed stream being less than that in the input gas flow stream, the $C_2$ hydrocarbons being acetylene ($C_2H_2$), ethylene ($C_2H_4$), ethane ($C_2H_6$), or any combination of the foregoing, the aromatics being benzene ($C_6H_6$), toluene ($C_7H_8$), naphthalene ($C_{10}H_8$), or any combination of the foregoing;

(d) removing, via the first membrane, at least some $H_2$ from the first gas flow volume by permeating hydrogen ions through the first membrane into the second gas flow volume and such that oxygen ions permeate through the first membrane from the second gas flow volume into the first gas flow volume so as to reduce coking of the first membrane;

(e) removing, via an aromatics separation device connected to receive the first processed stream from the first gas flow volume, at least some aromatics from the first processed stream so as to provide a second processed stream comprising $CH_4$ and $C_2$ hydrocarbons and to provide a first output stream comprising the removed at least some aromatics, a quantity of the aromatics in the second processed stream being less than in the first processed stream;

(f) providing the second processed stream to a third gas flow volume of a second membrane reactor, the second membrane reactor comprising the third gas flow volume, a fourth gas flow volume, and a second membrane separating the third gas flow volume from the fourth gas flow volume, the second gas flow volume having a second catalyst therein;

(g) providing, via a second gas supply, a second sweep gas to the fourth gas flow volume, the second sweep gas comprising $O_2$ or an oxygen-containing compound;

(h) converting, via the second membrane reactor, at least some $CH_4$ in the second processed stream provided to the third gas flow volume of the second reactors, so as to provide a recycle stream to a recycle line, the recycle stream comprising $C_2$ hydrocarbons and aromatics and such that a quantity of $CH_4$ in the recycle stream is less than in the second processed stream;

(i) removing, via the second membrane, at least some $H_2$ from the third gas flow volume by permeating hydrogen ions through the second membrane into the fourth gas flow volume and such that oxygen ions permeate through the second membrane from the fourth gas flow volume into the third gas flow volume so as to reduce coking of the second membrane; and (j) providing, via the recycle line comprising one or more fluid conduits, the recycle stream as at least part of the input gas flow stream to the first membrane reactor, wherein the removing of (d) provides autothermal operation of the first reactor via an exothermic reaction between the permeated hydrogen in the second gas flow volume and the $O_2$ or oxygen-containing compound in the second gas flow volume, and the removing of (i) provides autothermal operation of the second reactor via an exothermic reaction between the permeated hydrogen in the fourth gas flow volume and the $O_2$ or oxygen-containing compound in the fourth gas flow volume.

7. The method of claim 6, wherein the first catalyst, the second catalyst, or both the first and second catalysts comprise Fe@$SiO_2$.

8. The method of claim 6, wherein the first membrane, the second membrane, or both the first and second membranes comprise a perovskite-type oxide having a formula of $M'Ce_{1-x-y}Zr_xM''_yO_{3-\delta}$, where:

M' is a least one of Sr and Ba;

M'' is at least one of Ti, V, Cr, Mn, Fe, Co Ni, Cu, Nb, Mo, W, Pr, Nd, Pm, Sm, Eu, Gd, Tb, Dy, Ho, Er, Tm and Yb;

x is between 0.01 and 0.2, inclusive; and y is between 0.01 and 0.3, inclusive.

9. The method of claim 6, further comprising:

storing in a storage container, which is in fluid communication with the aromatics separation device, the aromatics in the first output stream.

10. The method of claim 6, wherein the aromatics separation device comprises a condenser, and the method further comprises liquefying the aromatics in the first output stream.

11. A methane conversion system comprising:
- a first reactor comprising first and second flow volumes separated by a first membrane;
- a first gas supply constructed to provide a first sweep gas to the second flow volume, the first sweep gas comprising $O_2$ or an oxygen-containing compound;
- an aromatics separation device connected to receive a first processed stream from the first flow volume and constructed to remove at least some aromatics from the first processed stream;
- a second reactor comprising third and fourth flow volumes separated by a second membrane; and
- a second gas supply constructed to provide a second sweep gas to the fourth flow volume, the second sweep gas comprising $O_2$ or an oxygen-containing compound,
wherein each of the first and second reactors are constructed to convert at least some $CH_4$ in the first and third flow volumes, respectively, such that a quantity of $CH_4$ at an outlet of the respective reactor is reduced as compared to at an inlet of the respective reactor and such that a processed stream from the respective outlet comprises $C_2$ hydrocarbons and aromatics, and
each of the first and second membranes is constructed to allow permeation of hydrogen ions therethrough, so as to remove at least some $H_2$ in the first and third flow volumes, respectively.

12. The methane conversion system of claim 11, wherein:
(a) the first reactor is constructed for autothermal operation;
(b) the second reactor is constructed for autothermal operation; or both (a) and (b).

13. The methane conversion system of claim 12, wherein each autothermal operation is provided by an exothermic reaction between permeated hydrogen and the $O_2$ or oxygen-containing compound in the respective flow volume.

14. The methane conversion system of claim 11, wherein:
(a) the first membrane is constructed such that oxygen ions permeate through the first membrane from the second flow volume into the first flow volume, so as to reduce coking of the first membrane;
(b) the second membrane is constructed such that oxygen ions permeate through the second membrane from the fourth flow volume into the third flow volume, so as to reduce coking of the second membrane; or
both (a) and (b).

15. The methane conversion system of claim 11, wherein at least a portion of the processed stream from the outlet of the second reactor is provided to the inlet of the first reactor.

16. The methane conversion system of claim 11, wherein:
(a) the first flow volume has a first catalyst therein;
(b) the third flow volume has a second catalyst therein; or
both (a) and (b).

17. The methane conversion system of claim 16, wherein the first catalyst, the second catalyst, or both the first and second catalysts comprise Fe@$SiO_2$.

18. The methane conversion system of claim 11, wherein:
the $C_2$ hydrocarbons comprise acetylene ($C_2H_2$), ethylene ($C_2H_4$), ethane ($C_2H_6$), or any combination of the foregoing, and the aromatics comprise benzene ($C_6H_6$), toluene ($C_7H_8$), naphthalene ($C_{10}H_8$), or any combination of the foregoing.

19. The methane conversion system of claim 11, wherein the first membrane, the second membrane, or both the first and second membranes comprise a perovskite-type oxide having a formula of $M'Ce_{13-x-y}Zr_xM''_yO_{3-\delta}$, where:
M' is a least one of Sr and Ba;
M" is at least one of Ti, V, Cr, Mn, Fe, Co Ni, Cu, Nb, Mo, W, Pr, Nd, Pm, Sm, Eu, Gd, Tb, Dy, Ho, Er, Tm and Yb;
x is between 0.01 and 0.2, inclusive; and
y is between 0.01 and 0.3, inclusive.

20. The methane conversion system of claim 11, wherein the aromatics separation device comprises a condenser constructed to liquefy the at least some aromatics.

* * * * *